US012612655B2

(12) United States Patent
Korani et al.

(10) Patent No.: US 12,612,655 B2
(45) Date of Patent: Apr. 28, 2026

(54) METHODS FOR SCREENING BIOLOGICAL SAMPLES FOR CONTAMINATION

(71) Applicant: Inguran, LLC, Navasota, TX (US)

(72) Inventors: Walid Korani, Madison, AL (US); Nader Deeb, Navasota, TX (US); Alan Mileham, Middleton, WI (US); Charles Michael Cowan, Middleton, WI (US)

(73) Assignee: Inguran, LLC, Navasota, TX (US)

( * ) Notice: Subject to any disclaimer, the term of this patent is extended or adjusted under 35 U.S.C. 154(b) by 706 days.

(21) Appl. No.: 17/384,390

(22) Filed: Jul. 23, 2021

(65) Prior Publication Data

US 2022/0025443 A1 Jan. 27, 2022

Related U.S. Application Data

(60) Provisional application No. 63/056,287, filed on Jul. 24, 2020.

(51) Int. Cl.
| | |
|---|---|
| *G16B 30/10* | (2019.01) |
| *C12Q 1/6806* | (2018.01) |
| *C12Q 1/6816* | (2018.01) |
| *C12Q 1/6827* | (2018.01) |

(52) U.S. Cl.
CPC ......... *C12Q 1/6816* (2013.01); *C12Q 1/6806* (2013.01); *C12Q 1/6827* (2013.01); *G16B 30/10* (2019.02)

(58) Field of Classification Search
CPC .. C12Q 1/6806; C12Q 1/6816; C12Q 1/6827; G16B 30/10
See application file for complete search history.

(56) References Cited

U.S. PATENT DOCUMENTS

| | | | |
|---|---|---|---|
| 10,262,755 B2 | 4/2019 | Babiarz et al. | |
| 2015/0197785 A1 | 7/2015 | Carter et al. | |
| 2017/0275629 A1* | 9/2017 | Lieberman | ........... C12N 15/115 |
| 2017/0275692 A1* | 9/2017 | Moreno | ............... C12N 5/0605 |
| 2018/0237838 A1 | 8/2018 | Sakarya et al. | |

(Continued)

FOREIGN PATENT DOCUMENTS

| | | | | |
|---|---|---|---|---|
| CN | 110444255 A | * | 11/2019 | ........... C12Q 1/6869 |

OTHER PUBLICATIONS

International Search Report And Written Opinion issued on Feb. 4, 2022 in related Appl. No. PCT/UA21/43027.

(Continued)

*Primary Examiner* — Gary Benzion
*Assistant Examiner* — Lisa Horth
(74) *Attorney, Agent, or Firm* — Ryan Christensen; Hashim Rahman

(57) ABSTRACT

The invention includes a method of screening a biological sample for contamination by sequencing a first biological sample at a first depth to generate a first nucleotide sequence; determining map coordinates for one or more homozygous loci in the first nucleotide sequence; sequencing a second biological sample at a second depth to generate a second nucleotide sequence, wherein the second depth is lower than the first depth; determining loci in the second nucleotide sequence at the determined map coordinates; and comparing the one or more homozygous loci in the first nucleotide sequence with the determined loci in the second nucleotide sequence.

18 Claims, 16 Drawing Sheets

Specification includes a Sequence Listing.

(56) References Cited

U.S. PATENT DOCUMENTS

2019/0010543 A1* 1/2019 Babiarz ............... C12Q 1/6848
2020/0157629 A1  5/2020 Babiarz et al.

OTHER PUBLICATIONS

Ion Torrent Amplicon Sequencing. Life Technologies Corporation. 2011.

Weber-Lehmann et al. "Finding The Needle in The Haystack: Differentiating "Identical" Twins In Paternity Testing And Forensics By Ultra-Deep Next Generation Sequencing." Forensic Science International: Genetics, vol. 9, 2014, pp. 42-46.

Kiessling et al. "Detection and Identification of Bacterial DNA In Semen." Fertility and Sterility, vol. 90, No. 5, Nov. 2008. pp. 1744-1756.

Jenkins et al. "Pre-Screening Method for Somatic Cell Contamination in Human Sperm Epigenetic Studies." Systems Biology in Reproductive Medicine. vol. 64, No. 2, 2018, pp. 146-155.

European Search Report and Written Opinion issued Aug. 6, 2024, in related EP Appl No. 21846199.4, filed on Jan. 19, 2023.

Office Action issued in counterpart New Zealand Application No. 796204, dated Sep. 23, 2025 (4 pages).

Office Action issued in counterpart Canadian Application No. 3189334, dated Oct. 3, 2025 (4 pages).

Xu, C., Wu, K., Zhang, J., Shen, H., & Deng, H. (2016). Low-, high-coverage, and two-stage DNA sequencing in the design of the genetic association study. Genetic Epidemiology, 41(3), 187-197. https://doi.org/10.1002/gepi.22015.

* cited by examiner

Figure 2A:
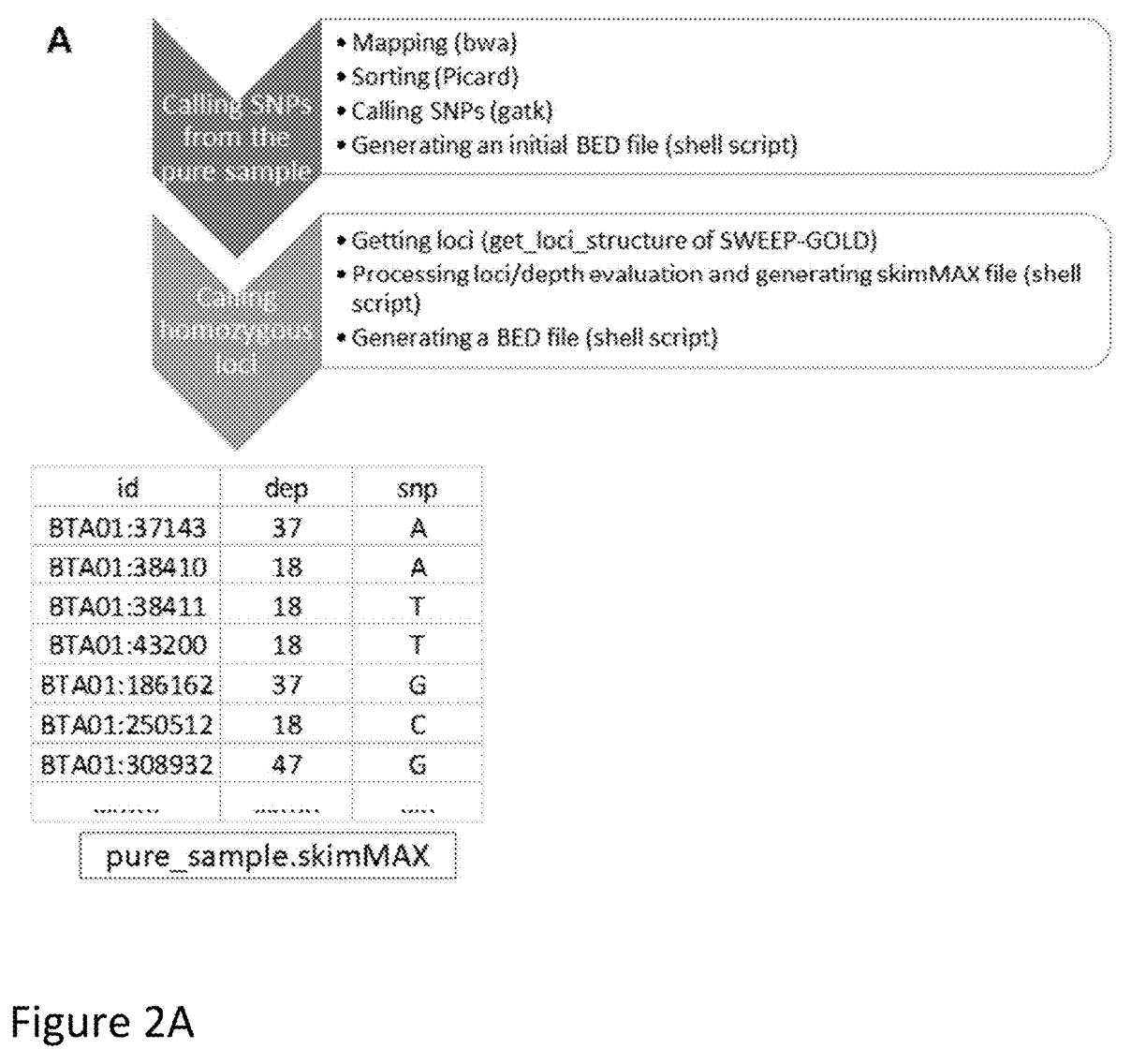

A

- Mapping (bwa)
- Sorting (Picard)
- Calling SNPs (gatk)
- Generating an initial BED file (shell script)

- Getting loci (get_loci_structure of SWEEP-GOLD)
- Processing loci/depth evaluation and generating skimMAX file (shell script)
- Generating a BED file (shell script)

| id | dep | snp |
|---|---|---|
| BTA01:37143 | 37 | A |
| BTA01:38410 | 18 | A |
| BTA01:38411 | 18 | T |
| BTA01:43200 | 18 | T |
| BTA01:186162 | 37 | G |
| BTA01:250512 | 18 | C |
| BTA01:308932 | 47 | G |
| ........ | ........ | ..... | pure_sample.skimMAX

- Mapping (bwa)
- Sorting (Picard)

- Getting loci (get_loci_structure of SWEEP-GOLD)
- Processing loci/depth evaluation (shell script)

| id | dep | snp |
|---|---|---|
| BTA01:37143 | 1 | A |
| BTA01:38289 | 1 | T |
| BTA01:38410 | 1 | A |
| BTA01:38411 | 1 | T |
| BTA01:39397 | 5 | TC |
| BTA01:43200 | 1 | T |
| BTA01:119902 | 2 | G |
| BTA01:119915 | 2 | T |
| BTA01:119930 | 2 | T |
| BTA01:119953 | 1 | C |
| ...... | ..... | ... | sample.skimMAX

C

D

| Level | Number | Mean | Std Dev | Std Err Mean | Lower 95% | Upper 95% |
|-------|--------|------|---------|--------------|-----------|-----------|
| A1 | 18,896 | 0.000976 | 0.003256 | 2.37e-5 | 0.00093 | 0.00102 |
| A2 | 18,896 | 0.011959 | 0.017212 | 0.00013 | 0.01171 | 0.01220 |
| A3 | 18,896 | 0.006291 | 0.015475 | 0.00011 | 0.00607 | 0.00651 |
| A4 | 18,896 | 0.011765 | 0.026731 | 0.00019 | 0.01138 | 0.01215 |
| A5 | 18,896 | 0.020465 | 0.044738 | 0.00033 | 0.01983 | 0.02110 |
| A6 | 18,896 | 0.040287 | 0.089996 | 0.00065 | 0.03900 | 0.04157 |
| A7 | 18,896 | 0.074116 | 0.160957 | 0.00117 | 0.07182 | 0.07641 |
| B1 | 18,896 | 0.096469 | 0.217740 | 0.00158 | 0.09336 | 0.09957 |

Fig. 7

| Level | | | | | | | | Mean |
|-------|---|---|---|---|---|---|---|------|
| B1 | A | | | | | | | 0.09646909 |
| A7 | | B | | | | | | 0.07411622 |
| A6 | | | C | | | | | 0.04028683 |
| A5 | | | | D | | | | 0.02046465 |
| A2 | | | | | E | | | 0.01195862 |
| A4 | | | | | E | | | 0.01176492 |
| A3 | | | | | | F | | 0.00629075 |
| A1 | | | | | | | G | 0.00097640 |

Fig. 8

SEQUENCE LISTING

<160> NUMBER OF SEQ ID NOS: 4

<210> SEQ ID NO 1
<211> LENGTH: 103
<212> TYPE: DNA
<213> ORGANISM: Bos taurus

<400> SEQUENCE: 1
gactgcccca acacttcttc ttgctgagct ctctcagcct ttttctcatg tgttttctca      60

-continued

```
tttcttgcca gctattcctt atgcatcgga gaaggcgatg gca                    103

<210> SEQ ID NO 2
<211> LENGTH: 92
<212> TYPE: DNA
<213> ORGANISM: Bos taurus

<400> SEQUENCE: 2
tcccatgaac cttagcatca caggcctccc tgtccatcaa caactcccag agttcactca     60
aactcatgtc cattgagtcg gtgatgccat cc                                  92

<210> SEQ ID NO 3
<211> LENGTH: 94
<212> TYPE: DNA
<213> ORGANISM: Bos taurus

<400> SEQUENCE: 3
tcccatgaac cttagcatca caggcctccc tgtccatcaa caactcccag agttcactca     60
aactcatgtc cattgagtcg gtgatgccat ccag                                94

<210> SEQ ID NO 4
<211> LENGTH: 111
<212> TYPE: DNA
<213> ORGANISM: Bos taurus

<400> SEQUENCE: 4
cgatcccatg aaccttagca tcacaggcct ccctgtccat caacaactcc cagagttcac     60
tcaaactcat gtccattgag tcggtgatgc catccagcca tcacatcctc t             111
```

METHODS FOR SCREENING BIOLOGICAL SAMPLES FOR CONTAMINATION

REFERENCE TO RELATED APPLICATIONS

This application claims the benefit of U.S. Provisional Patent Application No. 63/056,287 filed Jul. 24, 2020. The entire disclosure of which is incorporated herein by reference.

REFERENCE TO SEQUENCE LISTING

This application includes a sequence listing that has been submitted electronically in ASCII format and is hereby incorporated by reference in its entirety. Said ASCII copy, created on Jul. 16, 2025, is named ST-76 sequence listing.txt and is 1,180 bytes in size.

BACKGROUND OF THE INVENTION

The discovery of possible same-species contamination in biological samples is essential in various applications, e.g., for biological evidence in forensic or parentage cases, and for in vitro fertilization (IVF) and semen production for artificial insemination. Generally, this sort of contamination involves cells, and therefore DNA, from other individual(s) of the same species (cross-contamination), as well as the intended source individual (sometimes a close relative). Therefore, the evaluation of such contamination is challenging. Although genotyping and next-generation sequencing technology have established efficient, high throughput analyses in many biological applications, the implementation of these technologies to evaluate such cross-contamination using standard methods requires sequencing at a high depth. This is because the contaminating DNA is often very similar to that of the source individual and is often found in a very low quantity in the sample. Given that it is very costly, time consuming and resource intensive to identify low level contamination from another individual from the same species using conventional, high depth DNA sequencing strategies, there is a need for alternative methods for screening biological samples for contamination.

SUMMARY OF THE INVENTION

One aspect of the invention encompasses a method of screening a biological sample for contamination comprising sequencing a first biological sample at a first depth to generate a first sequence; determining map coordinates for one or more homozygous loci in the first sequence; sequencing a second biological sample at a second depth to generate a second sequence, wherein the second depth is lower than the first depth; identifying a nucleotide in the second sequence at the determined map coordinates; and comparing a nucleotide in the one or more homozygous loci in the first sequence with the identified nucleotide in the second sequence. In a specific embodiment, the step of identifying a nucleotide in the second sequence at the determined map coordinates comprises generating read data from the second sequence and mapping the read data from the second sequence. In a specific embodiment, the method further comprises the step of detecting a mismatch or a difference between the nucleotide in the one or more homozygous loci in the first sequence and the identified nucleotide in the second sequence. In another embodiment, the method further comprises the step of discarding the second biological sample based on the mismatch. In yet another embodiment, the method further comprises the steps of detecting a match between the nucleotide in the one or more homozygous loci in the first sequence and the identified nucleotide in the second sequence and further processing the second biological sample based on the match. In a further aspect of the invention, the second biological sample comprises a sperm cell sample and the step of further processing the second biological sample comprises sex-sorting the second biological sample, ablating sperm cells bearing an undesired sex chromosome in the second biological sample or cryopreserving sperm cells in the second biological sample. In a particular embodiment the homozygous loci comprise single nucleotide polymorphisms (SNPs).

Another aspect of the invention encompasses a method of screening a biological sample for contamination comprising sequencing a first biological sample at a first depth to generate a first sequence; determining map coordinates for one or more homozygous loci in the first sequence; sequencing a second biological sample at a second depth to generate a second sequence, wherein the second depth is lower than the first depth; sequencing at least one replicate of the first biological sample at the second depth to generate a third sequence; identifying a nucleotide in the second sequence at the determined map coordinates and a nucleotide in in the third sequence at the determined map coordinates; and comparing the nucleotide in the one or more homozygous loci in the first sequence with i) the identified nucleotide in the second sequence and ii) the identified nucleotide in the third sequence. In a specific embodiment, the step of identifying a nucleotide in the second sequence at the determined map coordinates and a nucleotide in the third sequence at the determined map coordinates comprises generating read data from the second sequence and read data from the third sequence and mapping the read data from the second sequence and the read data from the third sequence. Another aspect of the invention further comprises the step of detecting a mismatch between the nucleotide in the one or more homozygous loci in the first sequence and i) the identified nucleotide in the second sequence or ii) the identified nucleotide in the third sequence. In another embodiment, the method further comprises the step of discarding the second biological sample based on the mismatch. In yet another embodiment, the method further comprises the steps of detecting a match between the nucleotide in the one or more homozygous loci in the first sequence and i) the identified nucleotide in the second sequence or ii) the identified nucleotide in the third sequence and further processing the second biological sample based on the match. A further aspect comprises the method, the second biological sample comprises a sperm cell sample and the step of further processing the second biological sample comprises sex-sorting the second biological sample, ablating sperm cells bearing an undesired sex chromosome in the second biological sample or cryopreserving sperm cells in the second biological sample. In a particular embodiment the homozygous loci comprise single nucleotide polymorphisms (SNPs).

Another aspect of the instant invention encompasses detecting contamination in a biological sample using SNP analysis. By comparing SNP data obtained from a biological sample from an individual, using for example a SNP chip or array, and comparing the SNP data to the DNA sequence for the individual, one can determine whether the biological sample is contaminated with DNA from other individuals.

Yet another aspect of the instant invention encompasses detecting contamination in a semen sample from a non-human mammal by extracting a first set of omics data comprising one or more features from a reference cell sample; extracting a second set of omics data comprising the one or more features from the sperm cell sample; detecting a mismatch or difference between the first set of omics data and the second set of omics data. In a particular embodiment, the mismatch or difference comprises i) a difference in the quantity or concentration of a molecule (e.g., DNA, RNA, a protein or a metabolite) or ii) the presence or absence of a molecule (e.g., DNA, RNA, a protein or a metabolite). In a further aspect of the invention, the step of extracting a first set of omics data comprises obtaining DNA, RNA, a protein, a metabolite or any other molecule from the reference cell sample, or detecting or quantifying DNA, RNA, a protein, a metabolite or any other molecule in the reference cell sample. In specific embodiments, the RNA is comprised of mRNA, pre-mRNA, tRNA, rRNA, ncRNA, lncRNA, miRNA, siRNA, snoRNA, piRNA, tsRNA or srRNA. In a particular embodiment of the invention, the first set of omics data comprises a DNA sequence and the second set of omics data comprises a genotype. In a more particular embodiment, the genotype is an SNP genotype.

Another embodiment of the invention comprises a method of screening a biological sample for contamination comprising sequencing a first biological sample to generate sequence data; imputing a first sequence from the sequence data; determining map coordinates for one or more homozygous loci in the first sequence; sequencing a second biological sample to generate a second sequence; identifying a nucleotide in the second sequence at the determined map coordinates; and comparing a nucleotide in the one or more homozygous loci in the first sequence with the identified nucleotide in the second sequence.

Yet another embodiment of the invention comprises a method of screening a biological sample for contamination comprising sequencing a first biological sample to generate sequence data; imputing a first sequence from the sequence data; determining map coordinates for one or more homozygous loci in the first sequence; sequencing a second biological sample to generate a second sequence; identifying a nucleotide in the second sequence at the determined map coordinates; and comparing the nucleotide in the one or more homozygous loci in the first sequence with the identified nucleotide in the second sequence.

An additional method of the invention comprises a method of screening a biological sample for contamination comprising sequencing a plurality of biological samples from an individual to generate a plurality of sequences; compiling the plurality of sequences to generate a compiled sequence; determining map coordinates for one or more homozygous loci in the compiled sequence; sequencing a test biological sample from the individual to generate a test sequence; identifying a nucleotide in the test sequence at the determined map coordinates; and comparing a nucleotide in the one or more homozygous loci in the compiled sequence with the identified nucleotide in the test sequence.

An additional embodiment comprises a method for screening a non-human mammalian sperm cell sample for contamination comprising generating a reference call intensity for an allele that is homozygous for a given SNP from a reference cell sample; generating a test call intensity for the allele for the SNP from a test cell sample; and detecting contamination in the test cell sample by estimating the proportion of allele calls for the allele and for the alternate allele in the test cell sample.

Yet another embodiment of the invention comprises a method of screening a biological sample for contamination comprising determining or imputing a first nucleotide sequence for a first biological sample and a second nucleotide sequence for a second biological sample, the first biological sample and the second biological sample being from an individual of a species; identifying matched and mismatched loci between the first nucleotide sequence and the second nucleotide sequence; determining a matched loci count and a mismatched loci count from the identified matched and mismatched loci, wherein a sum of the matched loci count and the mismatched loci count constitutes a total loci count; calculating a ratio of the matched loci count to the total loci count or a ratio of the mismatched loci count to the total loci count. In a more particular embodiment, the matched and mismatched loci constitute homozygous loci. In an even further embodiment, the homozygous loci is an alternate to a reference sequence. In another embodiment, the reference sequence is obtained from a second individual of the species. For purposes of this embodiment, a matched locus means that the same nucleotide or nucleotides are present at that locus in each of the respective nucleotide sequences (for example, both nucleotide sequences have a G at position 100 of chromosome 1), and a mismatched locus means that the nucleotide or nucleotides at that locus are different in each of respective nucleotide sequences.

In any of the embodiments described herein, the term "sequence" may be understood to mean a nucleic acid, nucleotide, amino acid or protein, sequence unless otherwise specified. In such case where a sequence is an amino acid or protein sequence in any of the above embodiments, instead of identifying a nucleotide in such sequence, an amino acid or protein may be identified and then used for comparison.

BRIEF DESCRIPTION OF THE DRAWINGS

FIG. 2A is a flowchart showing how the sequencing data for a pure biological sample is processed in one embodiment of the invention.

FIG. 7 shows average contamination for treatment groups in Example 3.

FIG. 8 indicates that all levels of contamination were significantly different from the uncontaminated Al treatment group in Example 3.

DETAILED DESCRIPTION OF THE INVENTION

One aspect of the instant invention encompasses a method for identifying cross-contamination as low as 1% using a low depth sequencing strategy. The instant invention has been tested with biological samples cross-contaminated at levels of 1%, 5%, 10%, 20%, and 40%; and 1%, 2%, 3%, 4%, and 5%. The test results demonstrate high confidence of identifying contamination at 5% or above and indicated that the method is capable of detecting contamination levels down to at least 1%.

Figure 1A:
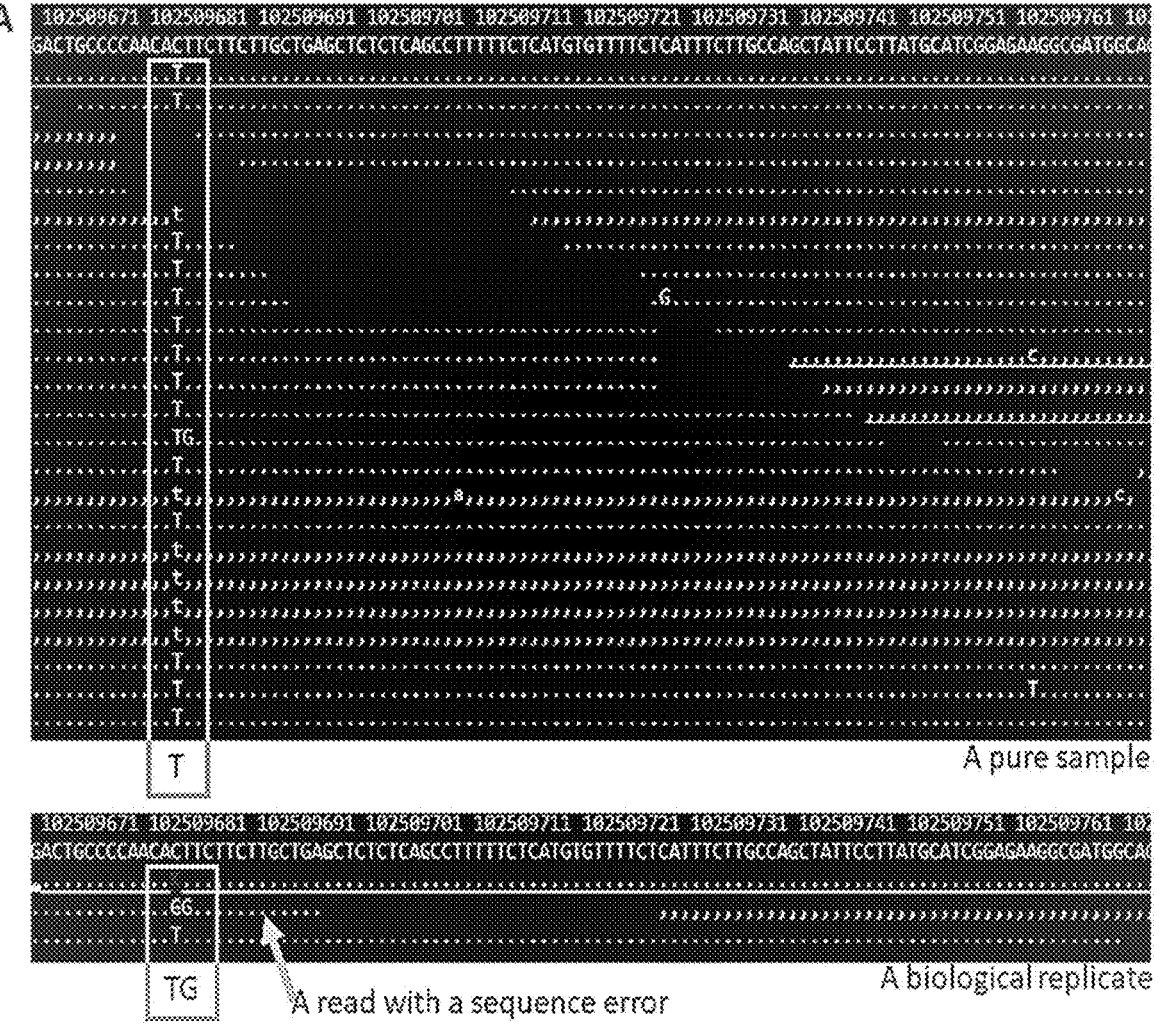
FIG. 1A represents a read of a pure biological sample and a read of a biological replicate (both generated using a reference genome comprising SEQ ID NO: 1) indicating a mismatch of a high confidence homozygous locus due to a sequencing error in the read of the biological replicate.
Figure 1B:
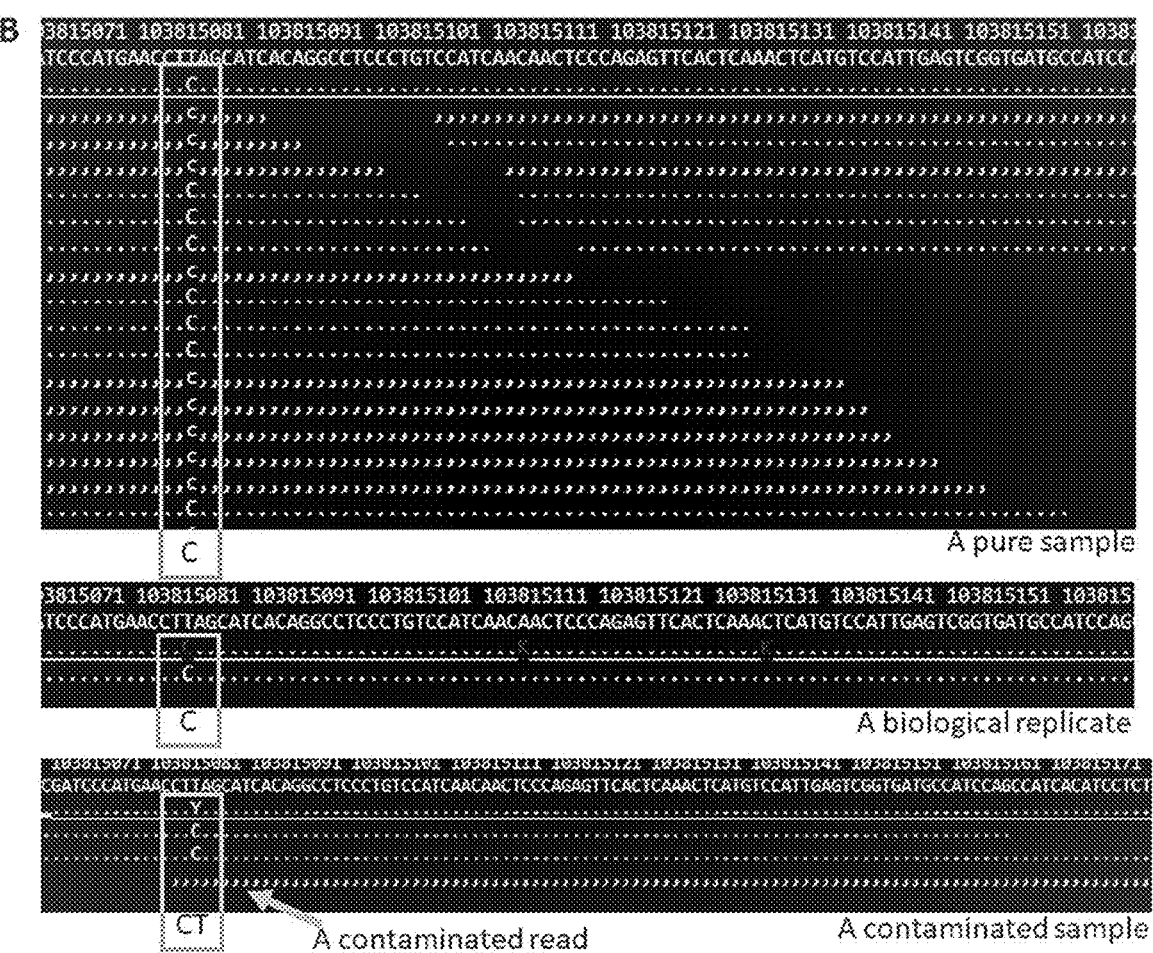
FIG. 1B represents a read of a pure biological sample (generated using a reference genome comprising SEQ ID NO:2), a read of a biological replicate (generated using a reference genome comprising SEQ ID NO:3) and a read of a contaminated sample (generated using a reference genome comprising SEQ ID NO:4) indicating a mismatch of a high confidence homozygous locus due to cross-contamination in the contaminated sample.

The following embodiment of the invention is presented by way of example only. A pure biological sample is nucleotide sequenced at a reasonably high depth (for example, in bovids, about 12×). Then, high confidence homozygous loci (HCHL) are extracted from this nucleotide sequence as mapped reads. Possible contaminated samples and at least three biological replicates of the pure sample are then sequenced at reasonably low depths (for example, in bovids, about 0.25×) relative to the depth at which the pure biological sample is sequenced. Next, the nucleotide(s) at the equivalent loci at the co-ordinates of the HCHLs are extracted from the mapped reads. Sequence reads from contaminating DNA will occur in proportion to the percentage of contaminating cells in a sample. HCHLs of the pure sample constitute reliable scaffolds for comparison of either possible contaminated samples or biological controls. Any mismatches (i.e., differences in a nucleotide, for example an "A" instead of a "G") at these loci will either result from sequencing errors, which can be estimated using the biological replicates (see FIG. 1A), or actual contamination (see FIG. 1B). Authentic contamination will show significantly higher mismatched read counts at HCHLs than the biological replicates at these loci.

The comparison will rely on the number of HCHLs that are variant between individuals of the intended source individual and the contaminating individual. Since there are many different HCHLs in the genome between individuals, even close relatives, there will be enough data to identify contamination. Each sample or replicate is considered as a binomial distribution. The frequencies of read counts at matched HCHLs are compared to the total read counts at all overlapping loci. The distribution of mismatched HCHLs between biological replicates should not be significantly different. However, the distribution of mismatched HCHLs in contaminated samples will show a significant difference. Obtaining Pure Biological Samples, Test Biological Samples and Biological Replicates In the context of the invention, a biological sample may be comprised of any biological material from an individual, including but not limited to tissue, cells, cellular structures, fluid and small or large molecules including but not limited to nucleic acids (e.g., DNA and RNA), amino acids, peptides, proteins, carbohydrates, lipids, metabolites, neurotransmitters, steroids, morphogens, colony stimulating factors, transcripts, enzymes, antibodies, cytokines, proteases, hormones, chemokines and growth factors. In a particular embodiment, a biological sample from an individual may be comprised of cultured tissue, cells or cellular structures, or fluid derived therefrom. A non-limiting list of cells that may be used in the invention is as follows: sperm cells, eggs, zygotes, blastomeres, stem cells, red blood cells, white blood cells, fibroblasts, bone cells, neural cells, skin cells including epithelial cells and lipocytes, One aspect of the invention comprises establishing or obtaining reference omics data, including for example a reference sequence, for an individual, by for example, using a pure biological sample from the individual. For purposes of the invention, a pure biological sample from an individual is free or substantially free of biological material from one or more other individuals of the same species (i.e., free from cross-contamination). In order to minimize the possibility that a pure biological sample is cross-contaminated, one embodiment of the invention comprises extracting omics data from the pure biological sample, such as a sequence, after collection of the pure biological sample from the individual, and optionally after extension or treatment with a supportive media, nutrients or preservatives and prior to further processing such as packaging, centrifugation, resuspension, cryopreservation, thawing, staining (e.g., with a DNA-selective dye), labeling (e.g., with a fluorescent or radiolabeled antibody or oligonucleotide) cell sorting (e.g., sex-sorting via flow cytometry), ablation, inactivation, cell or histological analysis (e.g., cell morphology, viability, motility and concentration assessments) and cell separation (e.g., via magnetic nanoparticles).

In another aspect of the invention, one or more biological replicates are established or obtained from a pure biological sample from an individual, for example, by removing a portion of the pure biological sample. A particular embodiment of the invention comprises establishing or obtaining one or more biological replicates by removing a portion of a pure biological sample after collection of the pure biological sample from an individual, and optionally after extension or treatment of the pure biological sample with a supportive media, nutrients or preservatives, and optionally, after or prior to further processing of the pure biological sample such as by packaging, centrifugation, resuspension, cryopreservation, thawing, staining (e.g., with a DNA-selective dye), labeling (e.g., with a fluorescent or radiolabeled antibody or oligonucleotide) cell sorting (e.g., sex-sorting via flow cytometry), ablation, inactivation, cell or histological analysis (e.g., cell morphology, viability, motility and concentration assessments) and cell separation (e.g., via magnetic nanoparticles).

In an alternative embodiment of the invention, one or more biological replicates are established or obtained from an individual independently from, but approximately simultaneously with, or from the same approximate source or situs in the individual as, a pure biological sample. For example, a biological replicate may be established or obtained from an individual within 20 minutes, 10 minutes, 5 minutes, 3 minutes, 2 minutes, or 1 minute of obtaining a pure biological sample from the individual, or from the same approximate source or situs in the individual from which the pure biological sample is obtained, for example from the circulatory system or lymphatic system of the individual, from an organ or appendage of the individual or from the skin of the individual. In a further embodiment, one or more biological replicates from an individual are extended or treated using media, nutrients or preservatives identical to those used to extend or treat a pure biological sample from the individual or are subjected to the same processing steps to which a pure biological sample from the individual is subjected.

An additional aspect of the invention comprises establishing or obtaining test omics data, including for example a test sequence, from a test biological sample from an individual. In one embodiment of the invention, a test biological sample is comprised of a portion of the pure biological sample.

In an alternative embodiment of the invention, a test biological sample is established or obtained from an individual independently from a pure biological sample from the individual, for example, by establishing or obtaining a test biological sample from an individual at a time different than the time at which a pure biological sample from the individual is established or obtained.

In some embodiments of the invention, a test biological sample from an individual may be extended or treated with supportive media, nutrients or preservatives that differ from the supportive media, nutrients or preservatives used to extend or treat a pure biological sample from the individual. Additionally, a test biological sample from an individual may be subjected to processing steps that a pure biological sample from the individual is not subjected to, for example, packaging, centrifugation, resuspension, cryopreservation, thawing, staining (e.g., with a DNA-selective dye), labeling (e.g., with a fluorescent or radiolabeled antibody or oligonucleotide) cell sorting (e.g., sex-sorting via flow cytometry), ablation, inactivation, cell or histological analysis (e.g., cell morphology, viability, motility and concentration assessments) and cell separation (e.g., via magnetic nanoparticles), or to a processing step that differs from a processing step to which a pure biological sample is subjected, e.g., staining with a different type or concentration of dye.

In certain embodiments, a test biological sample from an individual is established or obtained from a batch, or lot, of biological material from an individual. The batch or lot of biological material may in turn be comprised of one or more biological samples from the individual. In a specific embodiment, a batch or lot of biological material from an individual is comprised of a single biological sample from the individual, for example, a single ejaculate, a single blood sample or a single skin sample from the individual. In a specific embodiment of the invention, a batch or lot of biological material from an individual is subjected to one or more processing steps, for example, packaging, centrifugation, resuspension, cryopreservation, thawing, staining (e.g., with a DNA-selective dye), labeling (e.g., with a fluorescent or radiolabeled antibody or oligonucleotide) cell sorting (e.g., sex-sorting via flow cytometry), ablation, inactivation, cell or histological analysis (e.g., cell morphology, viability, motility and concentration assessments) and cell separation (e.g., via magnetic nanoparticles).

In one aspect of the invention, reference omics data, for example, a reference sequence, is compared against omics data obtained from a test biological sample to detect or determine if there any discrepancies between the two, which would indicate contamination in the test biological sample. As mentioned above, reference omics data may be obtained from a pure biological sample from an individual. Reference omics data may also be obtained or compiled from any other type of biological sample from an individual, including test biological samples and biological replicates. In one embodiment of the invention, the pure biological sample and the test biological sample to be compared are obtained from the same individual.

In one embodiment of the invention, reference omics data from an individual is obtained from a single biological sample from the individual, such as a pure biological sample. In a more particular embodiment, the reference omics data comprises nucleotide sequence data. In an even more particular embodiment of the invention, the nucleotide sequence data is obtained by sequencing a single biological sample at a depth of 1× or more.

Alternatively, reference omics data for an individual can be obtained by compiling omics data obtained from a plurality of biological samples from the individual. In a particular embodiment, the reference omics data comprises nucleotide sequence data. In an even more particular embodiment of the invention, the nucleotide sequence data is obtained by sequencing a plurality of biological samples from an individual at a depth of less than 1×. This sequence data is then compiled to generate a reference sequence. For example, 10 independent 1× sequences from an individual can be combined to give 10× coverage for the individual.

In another alternative embodiment of the invention, a reference nucleotide sequence for an individual can be imputed from a nucleotide sequence obtained from a single biological sample from an individual. In a particular embodiment, the nucleotide sequence data is obtained by sequencing a single biological sample from the individual at a depth of less than 1×. A reference sequence is then generated from this sequence data by imputation. Any method in the art for imputing nucleotide sequences can be used in the invention, including but not limited methods for imputing a nucleotide sequence from a low depth sequence obtained using next generation (short read) sequencing, such as provided by Gencove (New York, New York) or by AlphaGenes at the Roslin Institute (Scotland, UK).

In any of the above embodiments, one can detect contamination in a test biological sample by comparing reference omics data from the individual with test omics data obtained from the test biological sample.

Omics Data

In the context of the invention, omics data may include, but is not limited to, genomic, proteomic, transcriptomic, epigenomic, microbiomic or metabolomic data. In one embodiment of the invention, omics data is derived or obtained from molecules (small or large) or any other substances (ions, elements, etc.) obtained or extracted from a biological sample (e.g., a cell or tissue sample) or detected in the biological sample. Both the presence and the quantity of such molecules or substances within a sample may be determined. Any known method in the art for detecting, measuring, quantifying or assaying molecules or other substances may be used with the invention, including but not limited to molecular hybridization, immunohistochemistry, real time quantitative PCR, quantitative reverse transcription PCR, blotting, nucleotide sequencing, protein sequencing, nuclear magnetic resonance spectroscopy, mass spectroscopy, liquid chromatography, gas chromatography and electrophoresis. In a specific embodiment, a transcriptome may be profiled using a microarray.

In a particular embodiment, transcriptomic, proteomic or metabolomic data can be derived from RNA, proteins or metabolites, respectively, found within a biological sample. In certain embodiments, a biological sample may be obtained from amniotic fluid or directly from a fetus or embryo, including a fetus or embryo in utero or in vitro, in accordance with any of the methods described hereinabove. Such a cell or tissue sample may be cryopreserved and then subsequently thawed for extraction of DNA or RNA or to obtain proteins or metabolites for profiling or any molecules providing omics data.

In one embodiment of the invention, omics data comprises features. For example, for metabolomic data, each assayed or measured metabolite can constitute a feature. In one embodiment, a feature may simply comprise the presence or absence of a particular molecule or substance, e.g., the presence of a particular metabolite or transcript, or alternatively a feature may comprise the quantity of a particular molecule or substance, e.g., the quantity of a particular metabolite or transcript. For example, the quantity of glucose in a tissue or blood sample can comprise a feature.

With respect to genomic data, in various embodiments of the invention, genomic data may comprise DNA or RNA-related data obtained from oligonucleotide arrays or other hybridization assays, DNA sequence data including next-generation sequence data and long read sequence data, or RNA sequence data. In a specific embodiment of the invention, genomic data may be obtained from whole or partial genome sequencing using any technique known in the art. In addition to obtaining genomic DNA sequences, in other embodiments of the invention, RNA may also be sequenced, including messenger RNA (mRNA), precursor mRNA (pre-mRNA), transfer RNA (tRNA), ribosomal RNA (rRNA), non-coding RNA (ncRNA), long RNA, including long non-coding RNA (lncRNA) and small RNA, including micro RNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). In addition to sequencing such molecules, it is also contemplated that real time quantitative PCR or quantitative reverse transcription PCR may be used to quantify DNA or RNA in a sample.

DNA Extraction

One aspect of the invention encompasses methods for extracting DNA from a biological sample and genotyping or sequencing the extracted DNA. DNA may first be extracted and then amplified (via PCR, for example) so that there is a sufficient amount of DNA for genotyping or sequencing. The invention encompasses embodiments in which the amount of DNA extracted is very low, ranging from 1 ng/μl to 10 ng/μl (based on double strand DNA assays). Visualization using 1% agarose gels has shown the extracted DNA in some examples to be large, ≥23000 MW with little fragmented DNA.

For genomic analysis, approximately 1-200 ng of double stranded DNA should be extracted per sample DNA at concentration per sample of 1-50 ng/μl. In certain embodiments of the invention, only 1 ng/μl to 10 ng/μl of DNA are necessary for genomic analysis or sequencing. In a particular embodiment, less than 15 ng of DNA total is necessary for genomic analysis or sequencing.

By way of example, the following DNA extraction and amplification procedure may be used in certain embodiments of the invention. One skilled in the art will know that variations on this method exists and that this method should not be construed to limit the functionality or scope of the current invention. This method is illustrative only.

Fibroblast DNA is extracted from the contents of a 25-cm2 culture bottle by the salting-out procedure, with minor modifications (Miller et al., 1988; Biase et al., 2002). Fifty nanograms of genomic DNA is used in 25 μL of PCR mix (1 U Taq polymerase, 100 μM dNTP, 1 mM $MgCl_2$, 5 pmol of each primer) and amplified across 36 cycles using the following conditions: 93° C. for 3 min, 93° C. for 40 s, 58° C. for 40 seconds, 72° C. for 40 seconds, and 72° C. for 5 min.

In certain embodiments of the invention, DNA from amniocytes and mesenchymal stem cells can be extracted using the Purelink Genomic Kit Cat #K1820-00 (Invitrogen). In further embodiments, once the DNA is extracted, it can be put through a whole genome amplification protocol using the Illustra Genomiphi V2 DNA amplification kit (GE Lifesciences), which uses the phi29 DNA polymerase to amplify the genome.

In other embodiments of the invention the following DNA extraction procedure is employed.

Cells exposed to culture media often contain fetal calf serum. Due to high levels of DNase commonly found in fetal calf serum and the presence of cations that could catalyze the hydrolytic cleavage of phosphodiester linkage in DNA, an equal volume of a solution containing Tris-EDTA is added to the harvested cells to chelate cations essential for DNase activity. After adding the Tris-EDTA, the cell suspension is then stored in 1.5 ml microcentrifuge tubes at 4° C. until required for DNA extraction.

The 1.5 ml tubes containing cell suspension are spun at ≥10000×g in a microcentrifuge for 45 seconds to pellet cells. The suspension solution is pipetted off carefully so as not to remove pelleted cells. Approximately 50 μl of suspension solution is left in the tube. The tubes are then vortexed for 10 seconds to resuspend the cell pellets. 300 μl of Tissue and Cell Lysis Solution (Lucigen Corp.; Madison Wisconsin) containing 1 μl of Proteinase K (Lucigen Corp.; Madison Wisconsin) are then added to each tube and mixed. The tubes are then incubated at 65° C. for 30 minutes while making sure to vortex at 15 minutes. The samples are then cooled to 37° C. Afterwards 1 μl of 5 mg/μl RNase A (Lucigen Corp.; Madison Wisconsin) is added to each sample and then mixed. The samples are then incubated at 37° C. for 30 minutes. The samples are then placed in a 4° C. cooler for 5 minutes. 175 μl of MPC Protein Precipitation Reagent (Lucigen Corp.; Madison Wisconsin) are then added to each sample, and the samples are then vortexed vigorously for 10-15 seconds. The samples are then centrifuged in order to pellet debris for 8 minutes at ≥10000×g. The supernatant is then transferred to a clean microcentrifuge tube. 600 μl of cold (−20° C.) isopropanol is added to the supernatant. Each tube is then inverted 30-40 times. The DNA is then pelleted by centrifugation for 8 minutes in a microcentrifuge at ≥10000×g. The isopropanol is poured off without dislodging DNA pellet. The pellet is rinsed once with 70% ethanol and then the ethanol is carefully poured off so as not to disturb the DNA pellet. The residual ethanol is then removed with a pipette, and the DNA pellet is allowed to air dry in the microcentrifuge tube. Once dried, the DNA pellet is resuspended in 20 µl Tris-EDTA.

Genotyping

In one aspect of the invention, extracted and/or amplified DNA from a biological sample may be genotyped using SNP arrays or chips, which are readily available for various species of animals from companies such as Illumina and Affymetrix. For purposes of the invention, the term "genotyping" includes, but is not limited to, obtaining SNP and/or copy number variation (CNV) data from DNA. For purposes of the invention, the term "genotype" includes, but is not limited to, SNP and/or copy number variation (CNV) data obtained from DNA. Low density and high density chips are contemplated for use with the invention, including SNP arrays comprising from 3,000 to 800,000 SNPs. By way of example, a "50K" SNP chip measures approximately 50,000 SNPs and is commonly used in the livestock industry to establish genetic merit or genomic estimated breeding values (GEBVs). In certain embodiments of the invention, any of the following SNP chips may be used: BovineSNP50 v1 BeadChip (Illumina), Bovine SNP v2 BeadChip (Illumina), Bovine 3K BeadChip (Illumina), Bovide LD BeadChip (Illumina), Bovine HD BeadChip (Illumina), Geneseek® Genomic Profiler™ LD BeadChip, or Geneseek® Genomic Profiler™ HD BeadChip.

Nucleotide Sequencing

One aspect of the invention comprises nucleotide sequencing nucleic acids such as DNA or RNA. In certain embodiments of the invention, nucleic acid is extracted from a pure biological sample, a test biological sample and then nucleotide sequenced using any known method known in the art, including but not limited to Sanger sequencing and high throughput sequencing, which includes next generation (short read) sequencing and third generation (long read) sequencing. In one embodiment of the invention, one read with short read sequencing typically on average comprises about 100 to 300 base pairs, and one read with long read sequencing typically on average comprises about 15,000 base pairs. Nonlimiting examples of sequencing methods for use in the invention include single-molecule real time sequencing, ion semiconductor sequencing, pyrosequencing, sequencing by synthesis, combinatorial probe anchor synthesis, sequencing by ligation, nanopore sequencing, massively parallel signature sequencing, polony sequencing, DNA nanoball sequencing, heliscope single molecule sequencing and sequencing using droplet based microfluidics or digital microfluidics.

Sequencing Depth

In the context of the invention, sequencing depth, or coverage, refers to the average number of sequencing reads that align to, or cover, known reference bases. The sequencing coverage level (i.e., depth) typically determines whether variant discovery can be made with a certain degree of confidence at particular base positions. At higher depths, each base is coved by a greater number of aligned sequence reads, which means that base calls can be made with a higher degree of confidence. The Lander/Waterman equation allows one to calculate coverage/depth (C) based on read length (L), number of reads (N), and haploid genome length (G) as follows C=LN/G.

In one embodiment of the invention, for a given read length and genome length, one can increase or decrease sequencing depth by respectively increasing or decreasing the number of reads. Alternatively, in another embodiment of the invention, for a given number of reads and genome length, one can increase or decrease sequencing depth by respectively increasing or decreasing the read length.

In one embodiment of the invention, for detecting cross contamination in a test biological sample by comparing it to a pure biological sample, genome length is assumed to be constant across the test biological sample, the pure biological sample and any biological replicates. One can therefore increase or decrease sequence depth between the biological samples by varying the number of reads or the read length when sequencing. Accordingly, in one embodiment of the invention, to sequence a second biological sample at a lower depth than a first biological sample, one decreases either the read length or the number of reads for the second biological sample relative to the read length and the number of reads for the first biological sample.

Sequence Quality Scores

Sequencing quality scores measure the probability that a base is called incorrectly.

The sequencing quality score of a given base, Q, is defined by the following equation:

$$Q = -10 \log_{10}(e)$$

where e is the estimated probability of the base call being wrong.

Higher Q scores indicate a smaller probability of error. Lower Q scores can result in a significant portion of the reads being unusable. They may also lead to increased false-positive variant calls, resulting in inaccurate conclusions.

Read length refers to the number of base pairs sequenced from a DNA fragment. After sequencing, the regions of overlap between reads are used to assemble and align the reads to a reference genome, reconstructing the full DNA sequence. For example, a quality score of 20 represents an error rate of 1 in 100, with a corresponding call accuracy of 99%.

Deep sequencing of transcriptomes, also known as RNA-Seq, provides both the sequence and frequency of RNA molecules that are present at any particular time in a specific cell type, tissue or organ. Counting the number of mRNAs that are encoded by individual genes provides an indicator of protein-coding potential, a major contributor to phenotype.

Multiplex Sequencing

One embodiment of the invention encompasses evaluating a biological sample for contamination using multiplex sequencing. Multiplex sequencing allows large numbers of libraries to be pooled and sequenced simultaneously during a single run on sequencing instruments. Sample multiplexing is useful when targeting specific genomic regions or working with smaller genomes. Pooling samples exponentially increases the number of samples analyzed in a single run, without drastically increasing cost or time and reduces the cost per sample.

Individual identifier, or "barcode," sequences are added to each DNA fragment during next-generation sequencing, or long read sequencing, library preparation so that each read can be identified and sorted before the final data analysis. These barcodes, or index adapters, can follow one of two major indexing strategies. In one example of multiplex sequencing that may be used in the invention, in the first step, two DNA fragments from two different biological samples are each attached to a specific barcode sequence that identifies the biological sample from which it origi-nated. In the second step, libraries for each sample are pooled in parallel, with each new read containing both the fragment sequence and its sample identifying barcode. In the third step, barcode sequences are used to demultiplex, or differentiate, reads from each biological sample. In the final step, each set of reads is aligned to a reference sequence.

Screening a Test Biological Sample for Cross-Contamina-tion

Figure 2B:
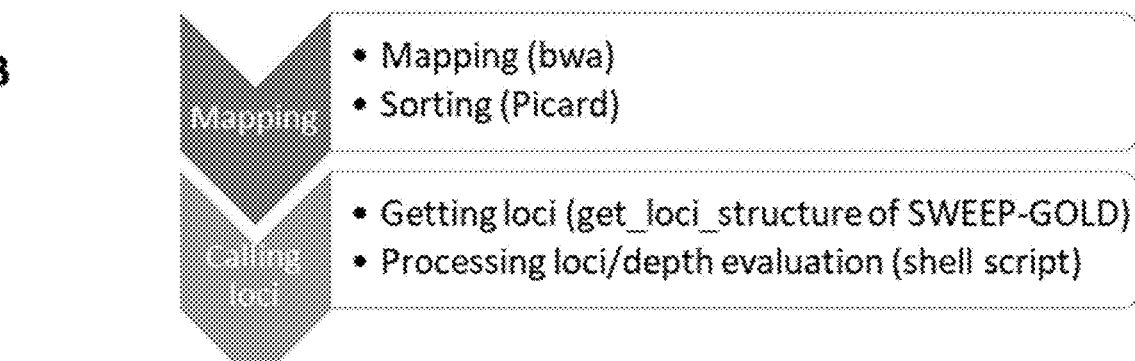
FIG. 2B is a flowchart indicating how sequencing data for a biological replicate or a test biological sample is processed in one embodiment of the invention.

One embodiment of the invention comprises a method of screening a test biological sample for cross-contamination. Referring generally to FIG. 2A, a pure biological sample is sequenced at a reasonable depth (for example, at least 12×) using for example a short read Illumina DNA sequencer (any DNA sequencing methodology can be used with the inven-tion. In a particular embodiment of the invention, the sequencer's error rate is less than the target contamination detection level). Single-end or paired-end reads can be used. The resulting fastq files are filtered for sequence quality and length. Any reliable aligner can be used in the invention to map the reads back to a reference genome or sequence, e.g., BWA (bio-bwa.sourceforge.net/; Li H. and Durbin R. 2009). The resulting BAM files are sorted and indexed using, for example, Picard tool (broadinstitute.github.io/picard/). The uniquely mapped high-quality reads are filtered for the subsequent steps (a filtered bam file). A SNP (single nucleo-tide polymorphism) caller, e.g., GATK (gatk.broadinstitute-.org/hc/en-us; McKenna et al., 2010), is then used to call possible variant loci compared with the reference genome. The co-ordinates of these loci are extracted from resulting VCF files into an initial BED file. Then the "get_loci_struc-ture" sub-module of SWEEP-GOLD (github.com/w-korani/SWEEP_GOLD) can be used to extract the exact nucleotide counts at each coordinate directly from a filtered bam file. The advantage of this step is that all nucleotides at these loci will be extracted, whereas SNP callers can drop some reads based on different criteria. In one embodiment of the inven-tion, any doubtful heterozygous loci should be filtered out. A locus that has a single alternate nucleotide as compared to the reference genome across all covered reads at that locus constitutes an HCHL. All HCHLs are extracted, SNPs are identified, and sequence depths are calculated and a BED file is generated.

DNA of biological replicates is extracted from a pure biological sample from an individual. In one embodiment of the invention, DNA of biological replicates is extracted and sequenced using the same methods as used for a possibly contaminated, test biological sample. In one embodiment of the invention, the sequence of a biological replicate is processed at low depth (for example, 0.25×, or 0.50×) and filtered bam files are generated as described above. Then the data is processed using "get_loci_structure" and the bed file of the pure biological sample. All loci, including any pos-sible heterozygous loci, are extracted.

Data Comparison and Statistical Model

An R script is written (ContTest.R) to compare each biological replicate with the pure biological sample. The counts of reads at matched and mismatched loci are calcu-lated. Then, Eval is calculated as follows.

$$Eval = \left( \frac{\sum_{k=1}^{n} x}{\sum_{k=1}^{n} x + \sum_{k=1}^{m} y} \right) * 100$$

x: reads at mis-matched loci y: reads at matched loci

The ratios of matched counts to total counts are used as frequencies for binomial distributions. All probabilities of possible difference are estimated for all biological replicates. In one embodiment of the invention, biological replicates show no significant differences. Then, the possibly contami-nated, test biological sample is serially compared to each of the biological replicates. Any significant difference will indicate contamination.

The contamination level has a positive correlation with Eval values, although Eval values are underestimated. This is because not all HCHLs are different between the source individual and the contaminating individual.

While the number of overlapping loci is affected by the sequence depth of the pure biological sample (or the sequence depth of any processed samples, including the biological replicates), there should be enough such loci to process for a reliable detection of contamination. Therefore, Loci Per Megabase (LPM) is calculated as described below. In one embodiment of the invention, LPM should be, for example, greater than or equal to 100. This would ensure that there is at least one HCHL per 10 Kilobases of the genome, thus providing good coverage across the genome.

$$LPM = \frac{\text{overlapped\_loci}}{\text{genome\_size}} * 10e6$$

Pipeline Packing

Figure 2C:
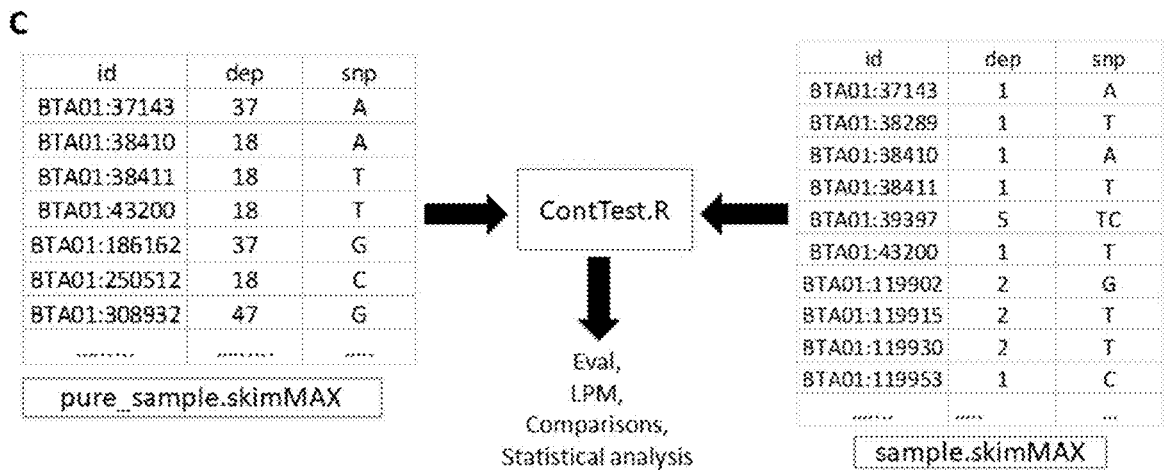
FIG. 2C is a flowchart showing how the processed sequencing data from a pure biological sample is compared to the processed sequencing data for a biological replicate or a test biological sample in one embodiment of the invention.
Figure 2D:
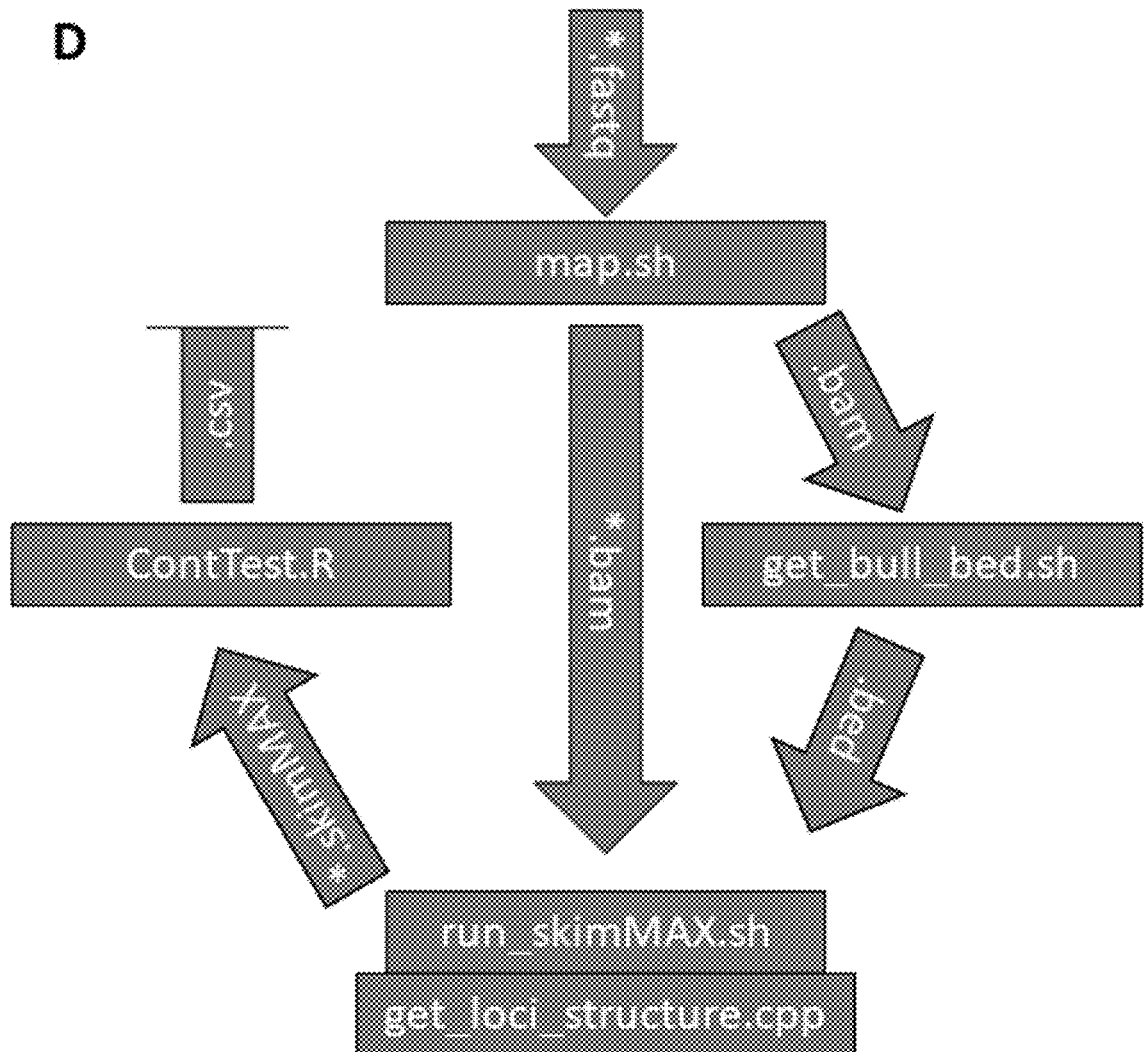
FIG. 2D is a flowchart of a pipeline of one embodiment of the invention.

Referring to FIG. 2, which represents one embodiment of the invention, the main infrastructure of the pipeline is written as a bash shell and R script; "map.sh" script is used to perform mapping, sorting, filtering, and indexing of bam files; "get_bull_bed.sh" is used to process and extract the coordinates of pre-filtered HCHLs only from pure biological samples; "run_skimMAX.sh" is used to extract the signature of pre-filtered HCHL coordinates from all bam files (includ-ing for pure biological samples, biological replicates, and test biological samples) using "get_loci_structure" sub-module of SWEEP-GOLD; finally, "ContTest.R" is used to hard filter HCHLs, calculate Eval and LPM values, process the comparisons, and run statistical analyses.

Example 1

Cross-contamination of sex sorted semen for AI is one of the major issues facing the livestock production. Fresh raw semen from a single ejaculate is diluted and sorted on different machines, then the sorted semen is recombined ahead of packaging. This practice increases the possibility of cross-contamination from previously processed ejaculates.

Two experiments were designed to test efficiency of the invention with different levels of contamination, as outlined in the following section.

A Wide Range of Contamination Set

Pure semen from a specific bull was sequenced at a depth of ~26× (the pure biological sample); six biological repli-cates were prepared from the same bull and sequenced at a depth of ~0.5×—three were used as biological replicates, and three were used as test biological samples with 0% contamination. Five pure semen samples were artificially contaminated using semen from another bull (contaminating individual) at 1%, 5%, 10%, 20%, and 40%. The latter five samples were repeated using DNA extracted from blood samples instead of semen to determine if the semen mixing could be biased to one of the two bulls involved.

Sequencing was carried out on Illumina instruments using paired-end reads. The resulting fastq files had slightly higher sequence depth than expected and so all replicates and sample files were sub-sampled in-silico to be at ~0.5×, while the pure sample was sub-sampled at ~12×.

Figure 3:
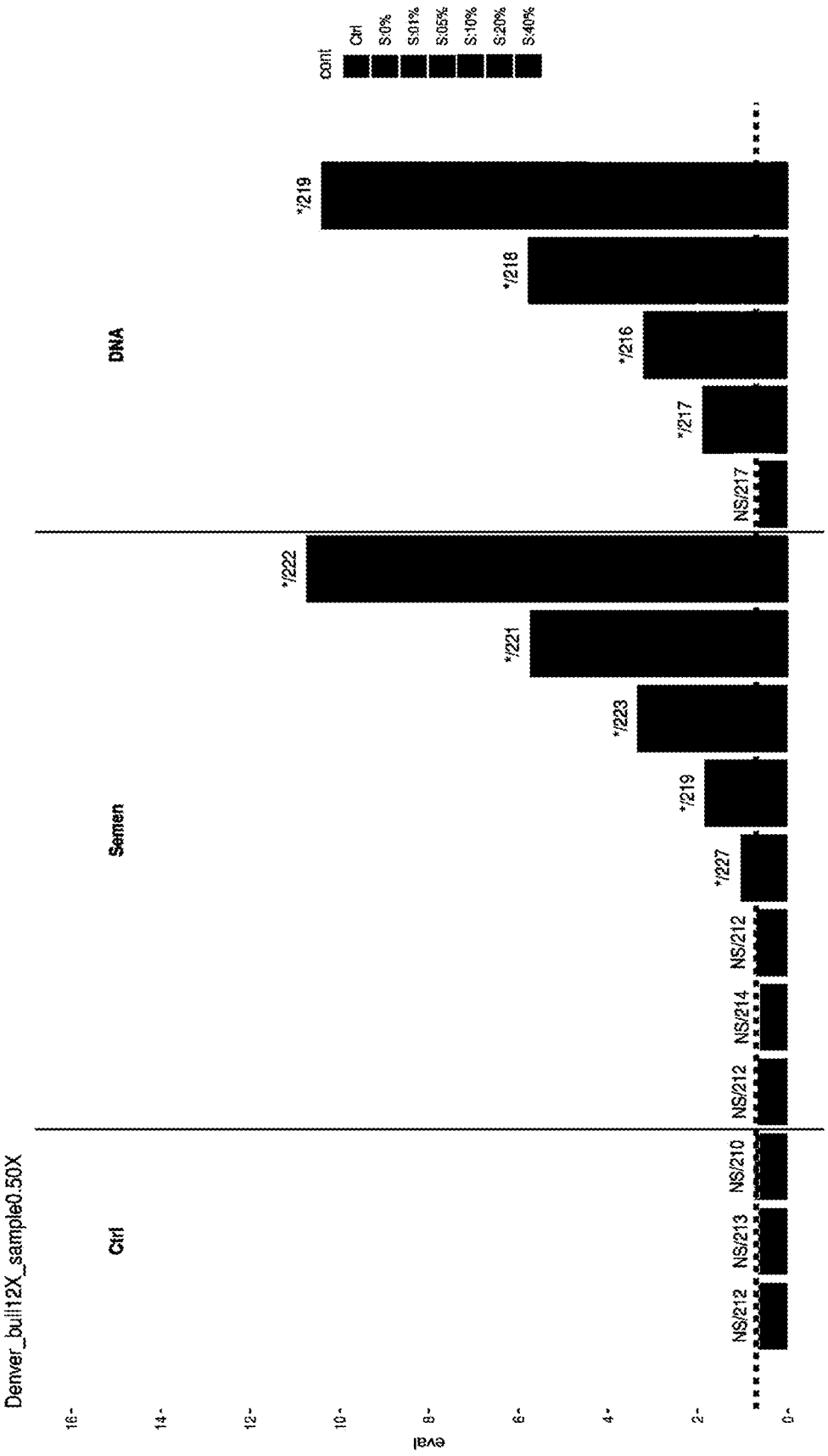
FIG. 3 is a graph showing the results of one of the methods of the invention for detecting cross-contamination in a test biological sample.

The method of the invention described in the section above entitled "Screening a Test Biological Sample for Cross-Contamination" was implemented, and the *Bos taurus* reference genome used for mapping read (www.ncbi.nlm-.nih.gov/assembly/GCF_000003205.7). The data showed no significant differences amongst the biological replicates, nor between the biological replicates and the zero contamination test biological samples. On the other hand, the biological replicates showed significant differences with all other contaminated test biological samples except the 1% contaminated samples, which gave Eval values not significantly different from the biological controls (sequence errors). Although the overall pattern reflects the contamination levels, Eval values were underestimated (see FIG. 3); this is expected, as not all HCHLs of pure samples are different from those of the contaminating bull. In other words, there is a level of similarity between the HCLCs of the two bulls as they are from the same species. LPM values were higher than 200 across the whole set, which indicates that the HCHLs were represented well across the entire genome (~ one locus per 5 Kilobase). This indicates that this method of the invention will have good reproducibility under these conditions.

Testing the Effect of Depth on the Results

The major factor affecting the Eval and LPM values is sequencing depth. This is because at higher depth, there are a higher number of overlapped loci. Therefore, the previous analysis was repeated multiple times using different combinations of data sub-sets to test how far sequencing depth of the pure biological sample or test biological samples affects analysis integrity and reproducibility.

Figure 4A:
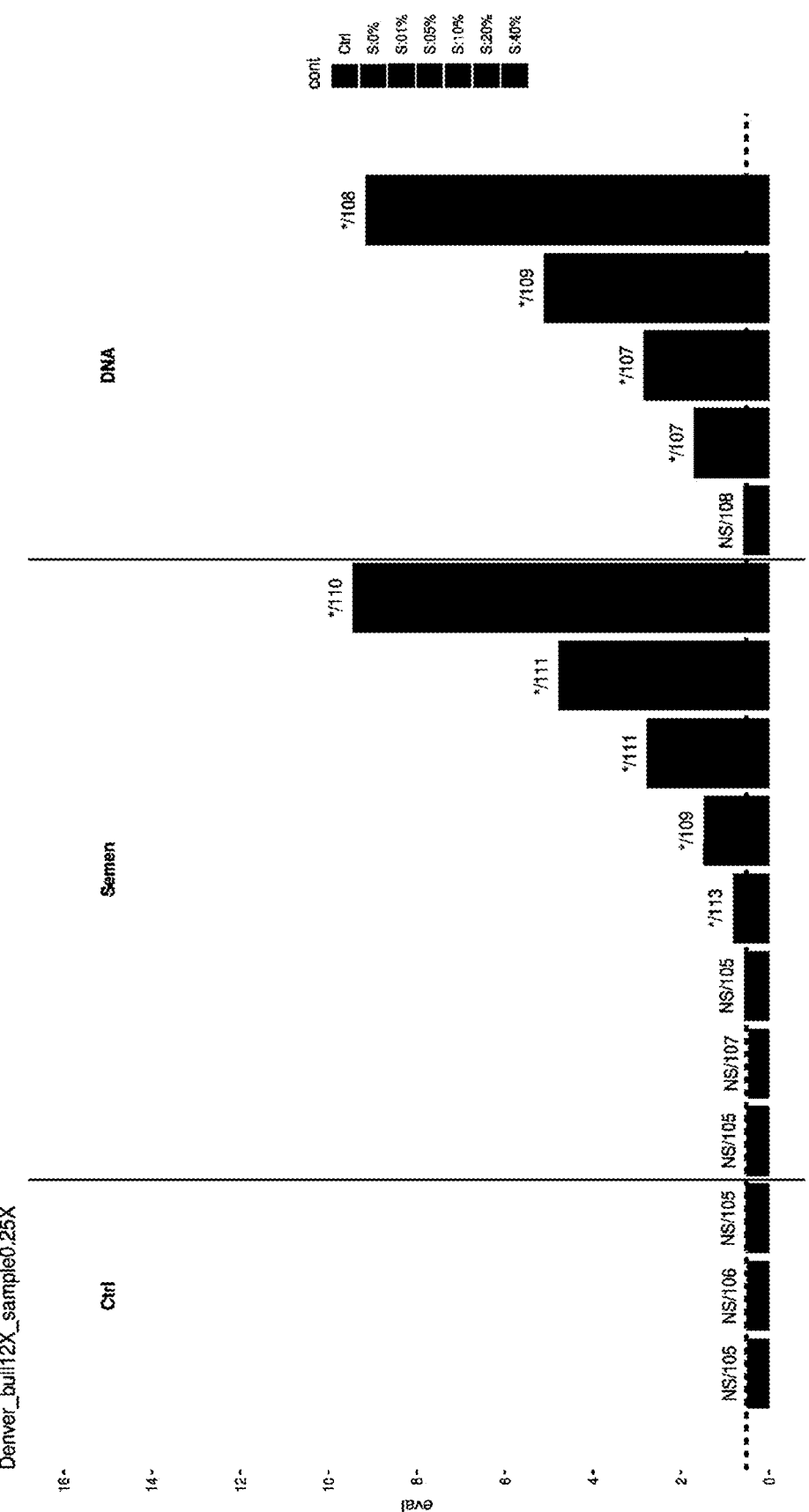
FIG. 4A shows the effect of lower sequencing depths on one of the methods of the invention with a first sample data set.
Figure 4B:
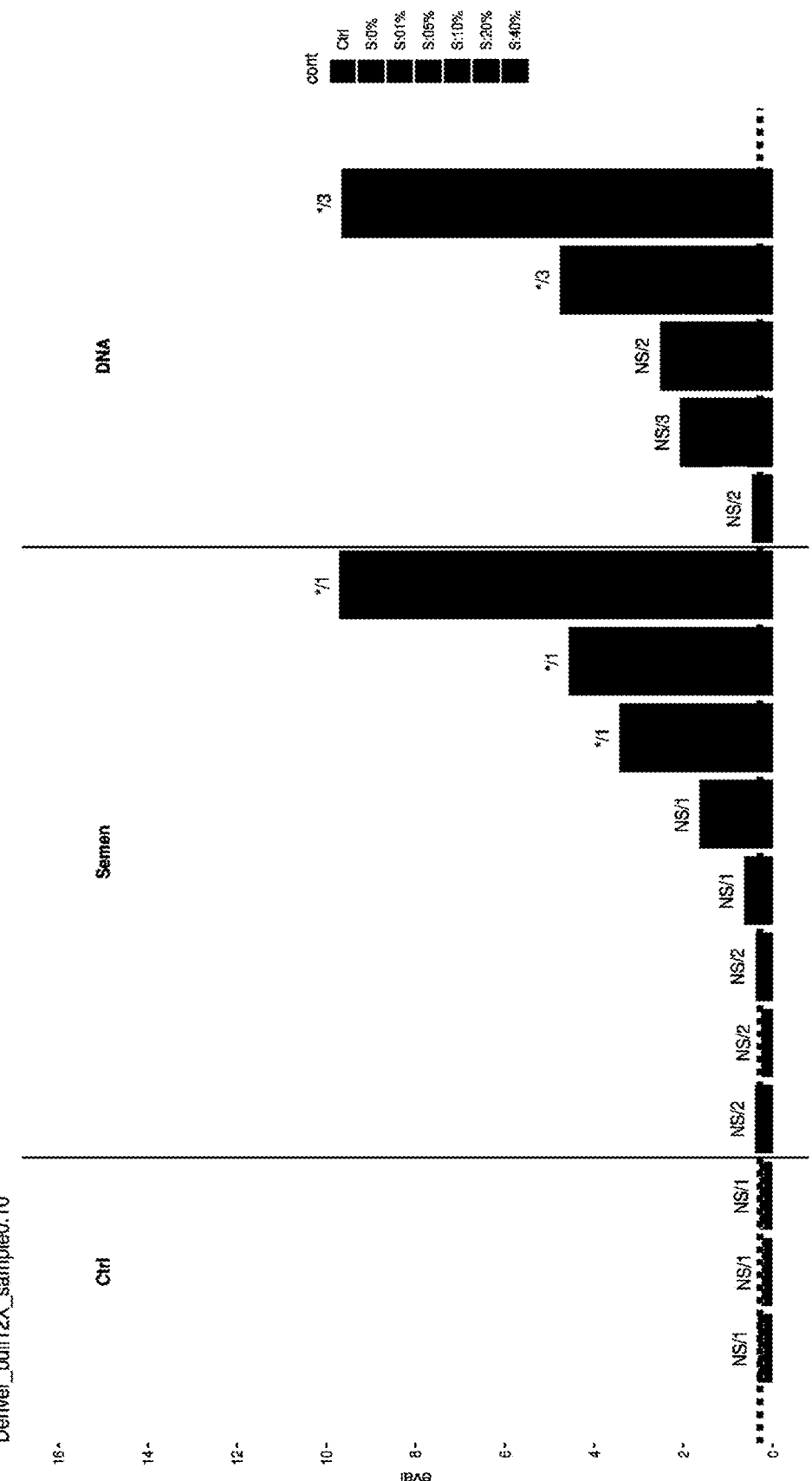
FIG. 4B shows the effect of lower sequencing depths on one of the methods of the invention with a second sample data set.

A sequencing depth of 12× depth was used for the pure biological sample while loci were extracted from a sub-set of in-silico reduced sample datasets of 0.25×, and 0.10× (see FIG. 4). The resulting data and statistical analysis were nearly identical. However, at a test biological sample sequencing depth of 0.10× there was a significant reduction in LPM values (1:3). This is because the overlapping loci do not have good coverage of the genome, and subsequently, the reproducibility of the analysis using this sequencing depth is low.

Figure 5A:
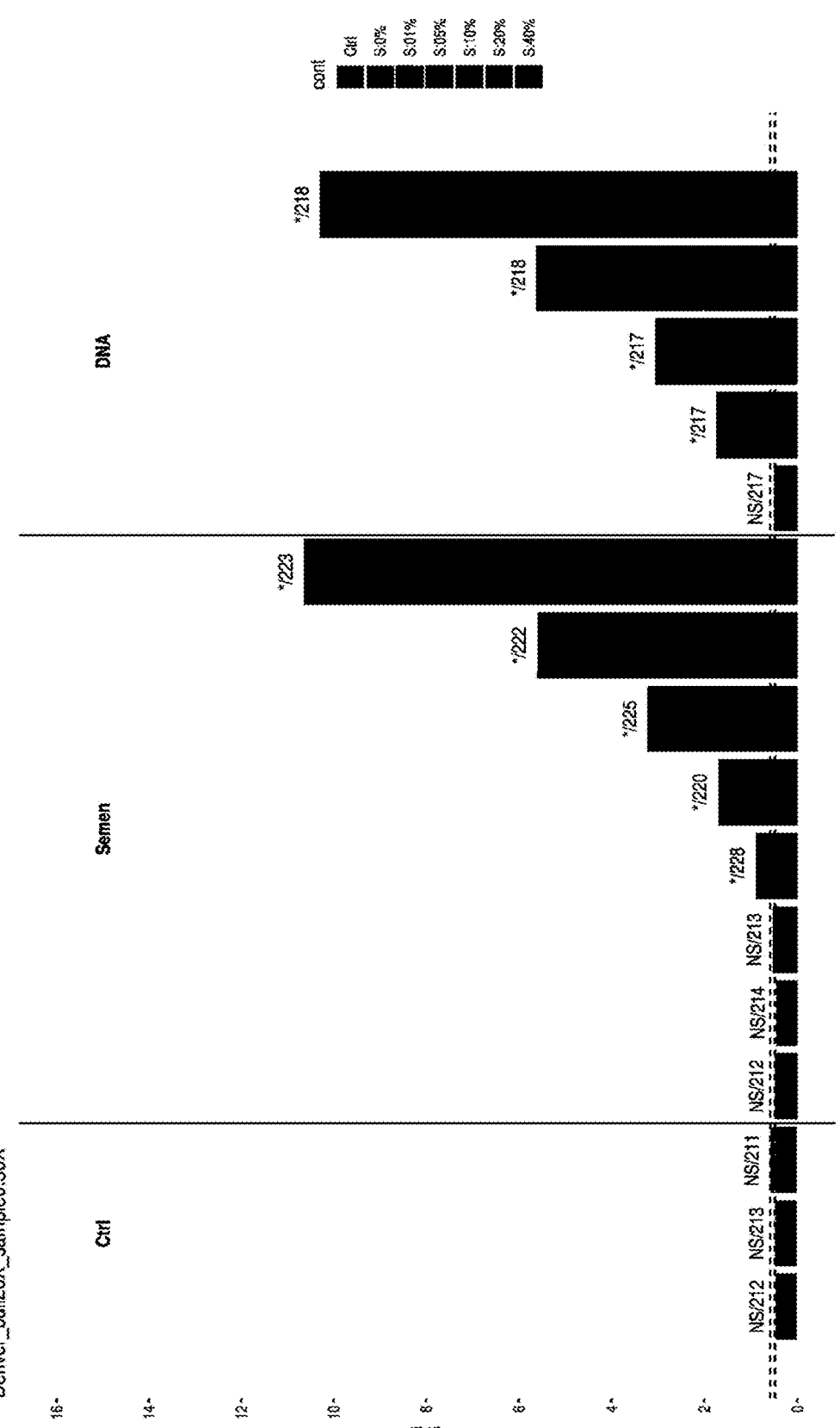
FIG. 5A shows the effect of a higher sequencing depth (26×) for pure biological samples.
Figure 5B:
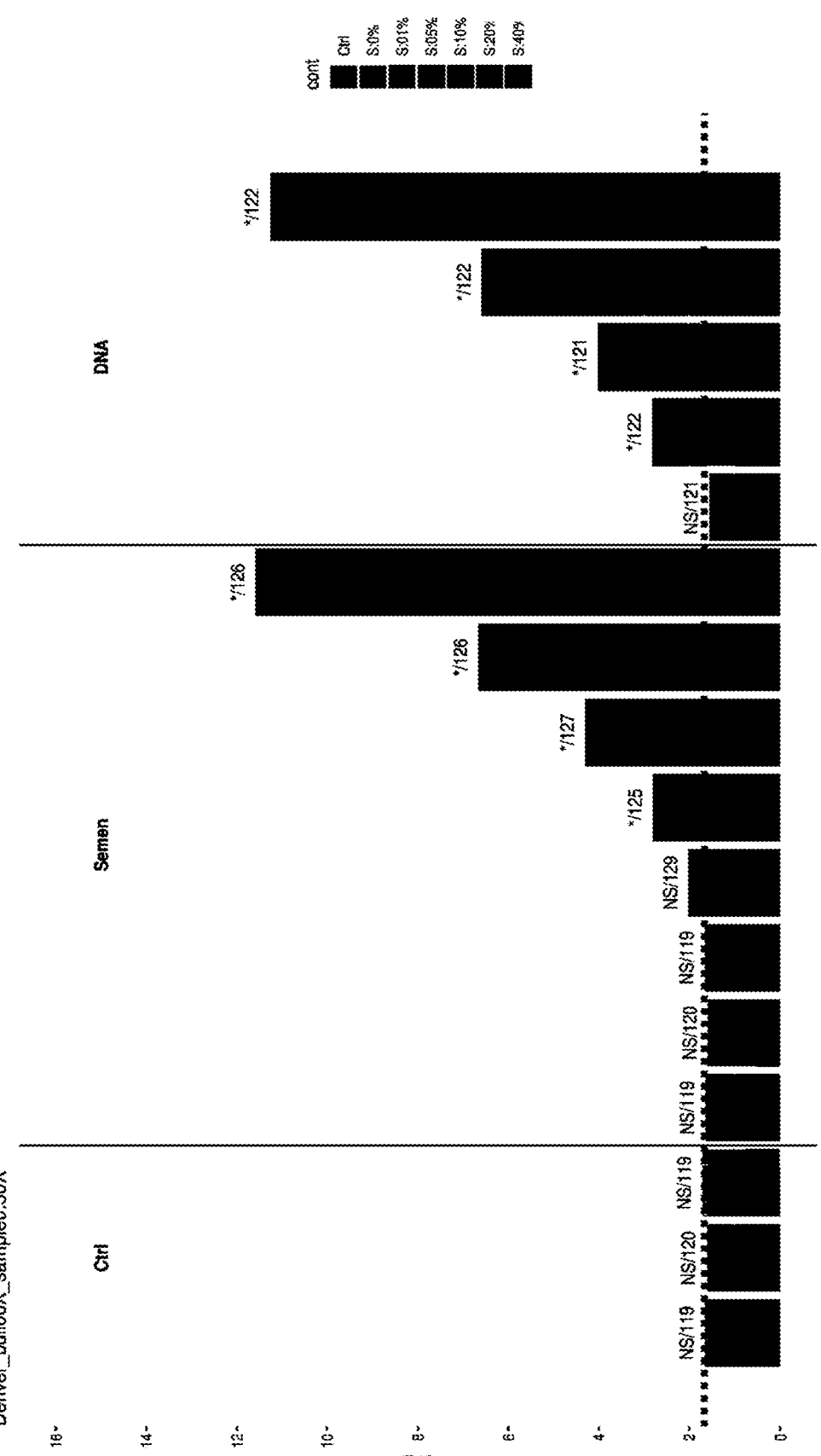
FIG. 5B shows the effect of a higher sequencing depth (6×) for pure biological samples.

In a similar scenario, the effect of pure biological sample sequence depth of 26×, or 6× was tested (see FIG. 5) using a test biological sample sequence depth of 0.5×. While LPM values were still above 100, the Eval values of the biological controls were increased in the pure sample at a sequencing depth of 6×.

A Narrow Range of Low Contamination Set

Semen from four bulls was mixed to create six levels of artificially contaminated semen ranging between 1% and 5%. These mixtures were then, analyzed using the method described above in this Example. The results showed that contamination could be detected at most levels of contamination. However, sometimes some contaminated samples did not show a significant difference to the pure sample or the gradient of contamination level was not as expected. The likely reason is that mixing semen at these low levels can result in significant experimental error, such as in the measurement of sperm concentration ahead of mixing, or in the pipetting, which leads to bias towards one of the bulls in the mixture.

This method is expected to have wide uses in different biological applications. In this Example, one method of the invention demonstrated high efficiency in the identification of contamination of 1% and above, using a sequencing depth of 12× for the pure biological sample and a sequencing depth of 0.3× for the biological replicates and the test biological samples.

Example 2

The objective of this Example was to evaluate the feasibility of using gene sequencing for semen quality control, specifically to (1) match semen identification with bull identification printed on straw and (2) identify mixture of semen from different bulls into the same straw.

Illumina® MiSeq® System with the TruSeq Bovine Parentage Kit was selected as the technology platform. Frozen, sexed semen samples were obtained from the inventory in Navasota. Straws were thawed and sperm concentration determined with a NucleoCounter. Different levels of semen mixtures, i.e. 0.1 to 5% (sperm Bull 1/sperm Bull 2) were obtained by combining different volumes of the 'contaminant semen' to the 'primary semen' to obtain samples normalized to 190-210 µl with approximately 4 million total sperm. DNA extraction/quantification/normalization and gene sequencing were performed according to the instructions provided by Illumina. Data analysis was performed using the platform provided by Illumina.

Experiment 1

Semen samples from 10 bulls were used in this experiment. Five sets of semen mixtures were produced including HO/HO, JE/JE, AN/AN and HO/RR at 0.1, 1 and 5% with unmixed semen serving as the basis for control (25 samples total).

Depth of sequences was 66-621×. The data analysis package allowed comparison of number of SNP discrepancies in know mixture samples when compared to the primary semen sample. Using this data analysis approach, the number of discrepancies observed in 5% mixture samples was considerably greater than in 0, 0.1 and 1% mixture samples (Table 1), indicating that this endpoint could be used to detect mixtures at 5% level.

TABLE 1

Number of SNP discrepancies in semen mixtures according to level of contamination when using the Illumina ® MiSeq technology platform (Experiment 1).

| Sample | SNP discrepancies 0.1% contamination | SNP discrepancies 1% contamination | SNP discrepancies 5% contamination |
|---|---|---|---|
| 1 | 2 | 7 | 42 |
| 2 | 7 | 4 | 18 |
| 3 | 4 | 7 | 15 |
| 4 | 6 | 6 | 15 |
| 5 | 7 | 13 | 36 |

Experiment 2

Semen samples from 10 bulls were used to produce semen mixtures. Five sets of semen mixtures were produced including at 1, 2, 3, 4 and 5% with unmixed semen serving as the basis for control (35 samples total).

Coverage depth was 816-1704.2× (average 1272.4×). The number of discrepancies in 2-3% mixture samples was clearly distinguishable from 1% mixture samples, indicating that this seems to be the sensitivity of the test.

TABLE 2

Number of SNP discrepancies in semen mixtures according to level
of contamination when using the Illumina ® MiSeq technology
platform (Experiment 2).

| Sample | SNP discrepancies 1% contamination | SNP discrepancies 1% contamination | SNP discrepancies 3% contamination | SNP discrepancies 4% contamination | SNP discrepancies 5% contamination |
|---|---|---|---|---|---|
| 1 | 0 | 10 | 15 | 20 | 28 |
| 2 | 2 | 9 | 12 | 23 | 25 |
| 3 | 2 | 9 | 26 | 36 | 39 |
| 4 | 3 | 3 | 10 | 20 | 27 |
| 5 | 3 | 13 | 18 | 26 | 30 |

Conclusion. Gene sequencing was successful in identify semen mixtures as low as 3% in all cases and as low as 2% in some cases.

Example 3

The objective of this Example was to test for potential sperm contamination using genotyping technology.

Typically, when contamination level is low, the usual clustering methods implemented by genotyping software fail to make the right genotyping call and the existence of additional alleles can be ignored as a background noise. Moreover, when the contamination level is high, genotyping software often fails to call those samples due to high background noise.

Genotypes are called based on observing a signal produced by the reaction of incorporating a base to the DNA template at the SNP position. While genotypes might not be called by the algorithm, the intensities of the signals are recorded by the genotyping software. The intensity of the signal, among other things, is a function of the number of copies of that specific allele. Therefore, we can use that quality to quantify the number of copies available in the sample of each allele (A and B) and determine if the observed number is different than expected, and therefore, if the sample is contaminated.

In this Example, we must have genotypes on record for all tested individuals (bulls). These are our reference genotypes to which we'll compare genotyping results from potential contaminated samples.

Eight different mixes of different levels of contaminations were created (Table 3) using conventional semen collections (i.e., not sex-sorted) from two highly related bulls. Samples were prepared, loaded into straws and shipped to the lab for genomic analysis. DNA was extracted using an organic extraction method and were genotyped using the Illumina LD4 SNP chip.

TABLE 3

| TREATMENT GROUPS | CONTAMINATION |
|---|---|
| A1 | 100% = CONTROL = 400 μL of Bull A |
| A2 | 99.5% OF BULL A + 0.5% OF BULL B |
| A3 | 99% OF BULL A + 1% OF BULL B |
| A4 | 95% OF BULL A + 5 % OF BULL B |
| A5 | 90 % OF BULL A + 10% OF BULL B |
| A6 | 75% OF BULL A + 25% OF BULL B |
| A7 | 50% OF BULL A + 50% OF BULL B |
| B1 | 100% BULL B |

Genotyping calls and allele intensities (X and Y values) on n=8 samples (treatments) and m=30,113 markers were received. Treatment A1 are the targeted samples—this represents the original genotyping calls from a tissue that is assumed to be uncontaminated. These are the reference genotyping calls used to evaluate the other treatment groups.

Treatment B1 is the contaminating bull and we have assumed that the identity and the genotyping calls are unknown. B1 does not have to be one sire—there can be 2 or more contaminants involved.

All markers for which A1 was homozygous (AA or BB) were selected and some markers were excluded based on the quality of their data (plot Y on X)→m=18,896.

While these markers are homozygous, the minor allele intensity is not zero (for example an AA call can have intensity X=0.9 and Y=0.08)—these intensities are referred to as RefX and RefY and their ratio as RefR (see Formula 1 below).

RefR=If(

:RefGN=="AA",:RefY/(:RefX+:RefY),

:RefGN=="BB",:RefX/(:RefY+:RefX));  Formula 1:

The RefR values were used to adjust the intensities for all samples (AdjX and AdjY, see Formula 2 below).

AdjX=If(

:RefGN=="AA",:X,

:RefGN=="BB",:X−:Y*:RefR);

AdjY=If(

:RefGN=="AA",:Y−:X*:RefR,

:RefGN=="BB",:Y);  Formula 2:

And finally, the level of contamination was estimated using the minimum of AdjX and AdjY (see Formula 3 below).

Figure 6A:
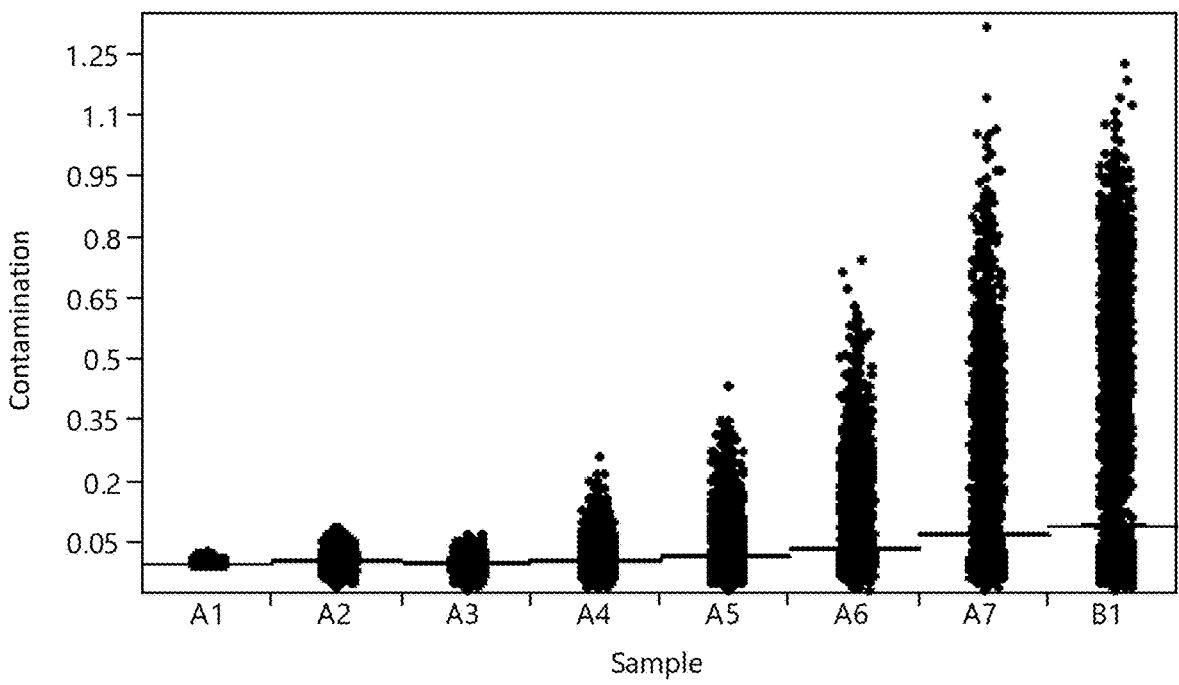
FIG. 6A shows the distribution of estimated levels of contamination for test biological samples in Example 3.
Figure 6B:
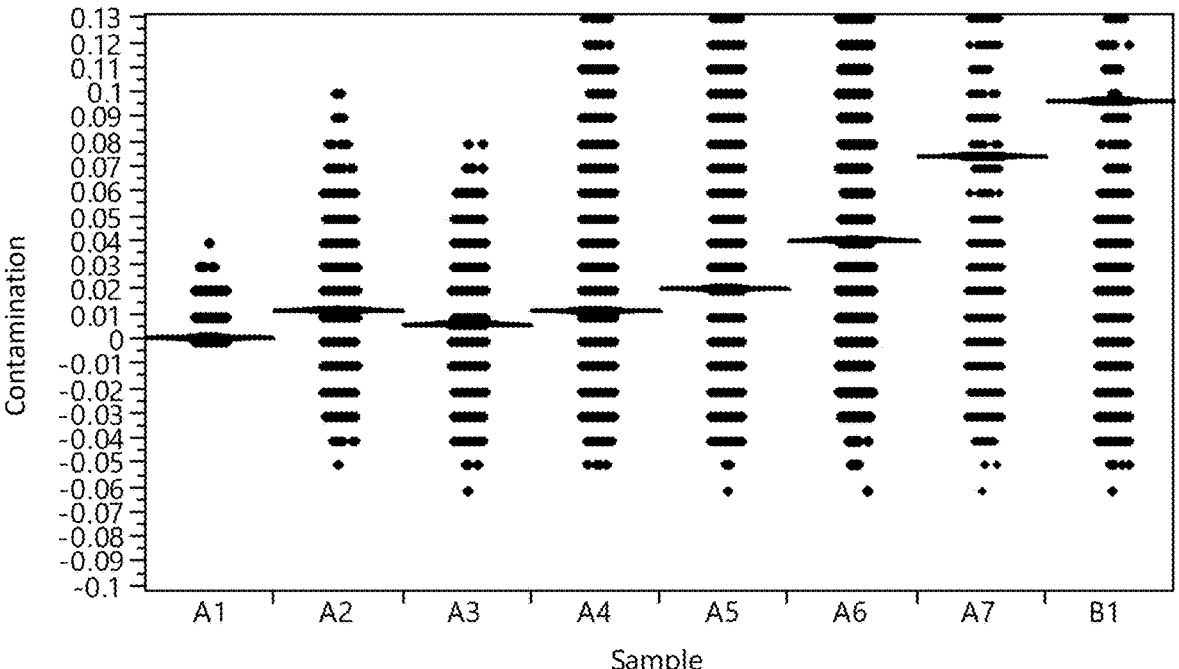
FIG. 6B shows a zoomed-in view of the distribution of estimated levels of contamination for test biological samples in Example 3.

Contamination=Min(:AdjX,:AdjY);  Formula 3:

The level of contamination (as calculated using Formula 3) was compared across all samples. Distribution of the estimated levels of contamination for all samples using all markers (m=18,896) is plotted in FIGS. 6A and 6B. Average contaminations are listed in FIG. 7. Results from all pairwise comparisons testing (Tukey test, alpha=0.05) are listed in FIG. 8. Average contamination level was under-estimated using this approach (see FIG. 7). However, all levels of contamination were significantly distinguished from the uncontaminated A1 sample (see FIG. 8).

Example 4

Following imputation, each sample in the following Example was evaluated for the number of single nucleotides polymorphism (SNPs) and categorized as either "11" (homozygous reference), "22" (homozygous alternative), or "12" (heterozygous) for each SNP, where homozygous reference means for a particular SNP, the only identified nucleotide in the sample is the same nucleotide in a reference sequence; homozygous alternate means for a particular SNP, the only identified nucleotide in the sample is a different nucleotide in the reference sequence; and heterozygous means for a particular SNP, two different nucleotides are identified in the sample.

The total number of SNPs called in the Example ranged from 51,167,348 to 56,971,984 with a mean of 56,625,560 and a median of 56,699,089 SNPs. Then all samples from an animal were contrasted with each other. For example, if an animal had 4 samples (A, B, C and D) sequenced and imputed, calls of 11, 12 and 22 are compared against each other for all 9 possible combinations.

Example of counts for samples A and B are shown in Table 4, below.

TABLE 4

Examples of counts for samples A and B

| | | Sample A | | |
| | | 11 | 12 | 22 |
|---|---|---|---|---|
| Sample B | 11 | N00 | N01 | N02 |
| | 12 | N10 | N11 | N12 |
| | 22 | N20 | N21 | N22 |

If Sample A and B are indeed sequences of the same individual with no DNA from a different individual (contamination), the two samples A and B will have identical genotypes calls. In other words, most calls will be contained in the boxes be in the diagonal starting from the upper left box (N00) to the lower right box (N22) in Table 4 and all off-diagonal cells will be zero. In a similar way all 4 samples are compared: A vs B, A vs C, A vs D, B vs C, B vs D, and C vs D.

Due to imputation accuracy and sequencing errors, the off-diagonal boxes in Table 4 will contain some calls (i.e., will not be zero). Therefore, the method in this Example consists of sampling 3 or more independent DNA samples from an uncontaminated source (any tissue type that contains DNA), and then using the comparison between the uncontaminated samples to establish a reference or a base line. These samples are used to calculated a median as shown below.

It was found that the count of the homozygote alternative (N22) is affected the most from any contamination (inclusion of DNA from a different sample). Thus, the number of calls contained in box N22 in contaminated samples is reduced significantly compared to two independent replicates from the same animal with no contamination. While in this Example N22 was used in the calculations, other categories (e.g., N00 or N11) either exclusively or in combination with N22 may be used in the calculations.

Among the uncontaminated samples, M is calculated as follows:

$$M = (1/(N22/N\text{Total})))$$

Where Ntotal=(Sum (N00, N10, N20, N01, N11, N21, N02, N12, N22)

Median=(Col Median (:M)))

Then the median of M calculated based on uncontaminated samples is used to adjust the contamination level of test samples as follows:

$$P = (1/(N22/N\text{total}) - \text{Median}))$$

Using this methodology, a validation trial was conducted as follows:

Bulls: Two bulls, A and B

Replicates: Three replicates: R1, R2, R3

Contamination levels: 10 different levels: 0%, 1%, 2%, 3%, 4%, 5%, 6%, 8%, 10%, 20%, where 1% contamination contained 99% sperm cells from Bull A and 1% from Bull B, 2% contamination contained 98% sperm cells from Bull A and 2% from Bull B, and so forth.

From a single ejaculate from Bull A and B separately, samples of sperm cells were diluted to contain equal number of cells, then samples from Bulls A and B were mixed by volume to create the above mentioned contamination levels in three separate batches (replicates). The three replicates with 0% contamination were used to establish a base line and calculate the median (see above). Then each contamination level within a replicate was compared to the 3 replicates with 0% contamination. For example, the 1% contamination (containing 99% of the sperm cells from bull A and 1% of the cells from bull B, by count) from replicate 1, was contrasted against 0% contamination three times:

1% R1 vs 0% R1

1% R1 vs 0% R2

1% R1 vs 0% R3

Figure 9:
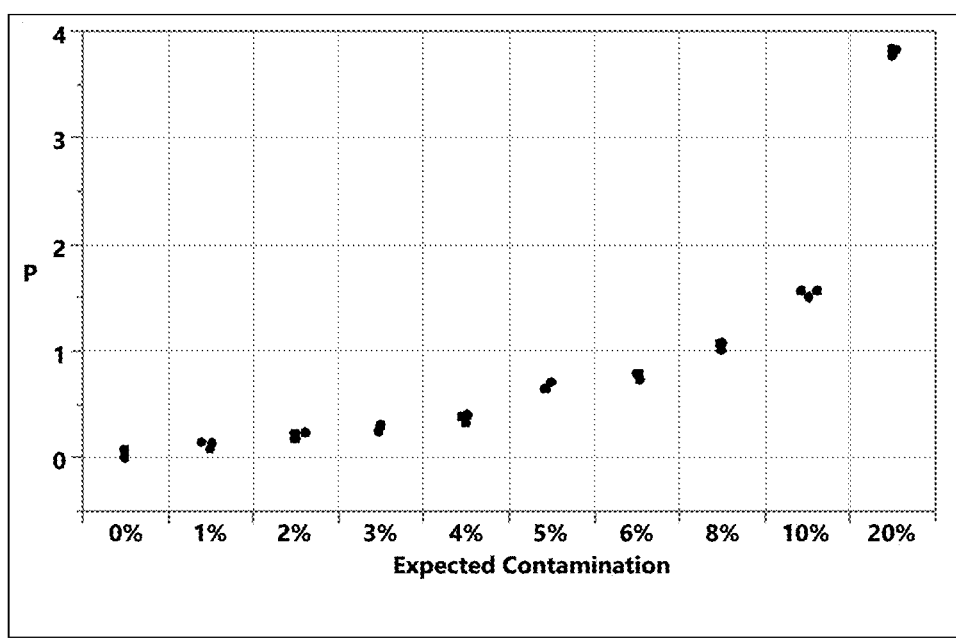
FIG. 9 shows a plot of P values at various levels of contamination for a first replicate using sperm from Bull A and Bull B.
Figure 10:
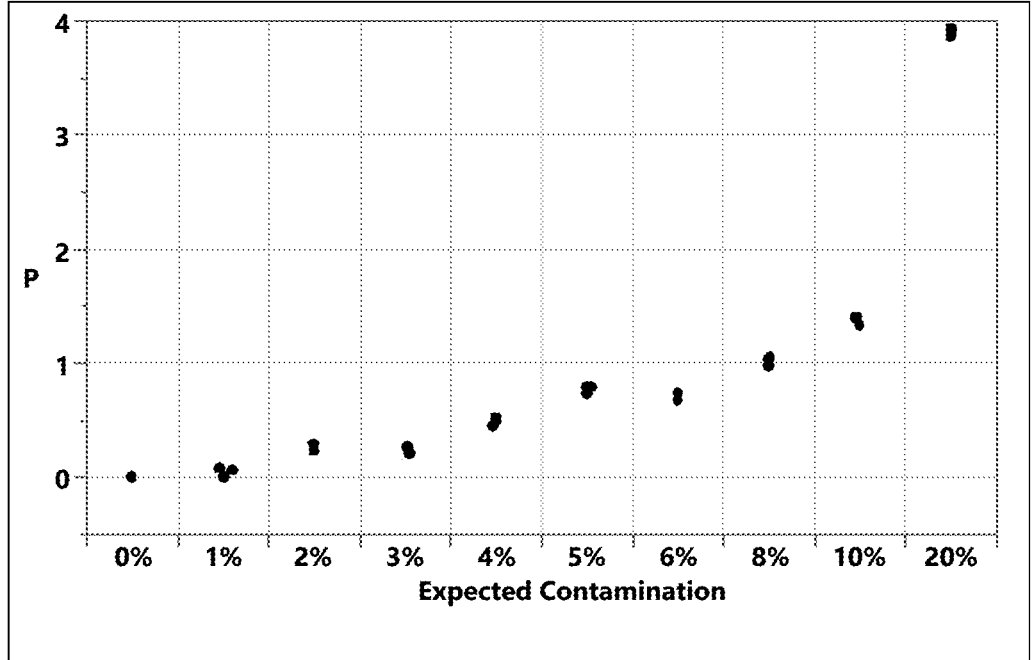
FIG. 10 shows a plot of P values at various levels of contamination for a second replicate using sperm from Bull A and Bull B.
Figure 11:
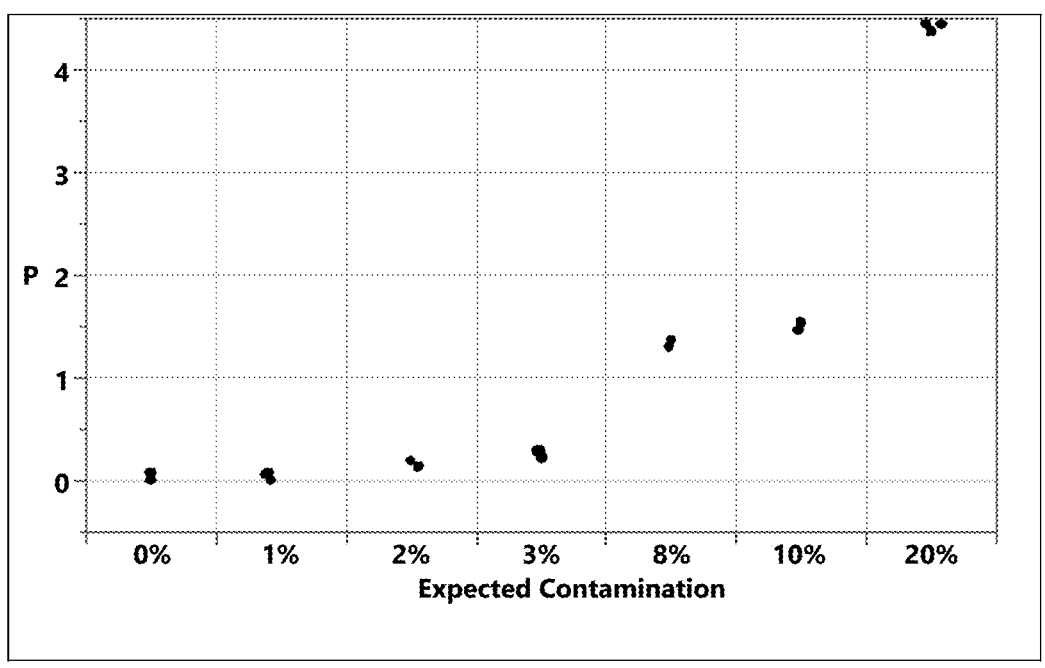
FIG. 11 shows a plot of P values at various levels of contamination for a third replicate using sperm from Bull A and Bull B.

A P value (see above) was calculated for each comparison. FIGS. 9, 10 and 11 show the scatter plots of P by expected contamination level and replicate. FIG. 9 shows replicate 1, FIG. 10 shows replicate 2 and FIG. 11 shows replicate 3.

Tables 5, 6 and 7 below show the result of means comparisons for replicates 1, 2 and 3, respectively, in which calculated P values were compared with a control using Dunnett's Method, in which the Control Group=0% contamination.

TABLE 5

Study 1 LSD (Least Significant Difference) Threshold Matrix Replicate 1

| Level | Abs(Dif)-LSD | p-Value |
|---|---|---|
| 20% | 3.673 | <.0001* |
| 10% | 1.41 | <.0001* |
| 8% | 0.913 | <.0001* |
| 6% | 0.63 | <.0001* |
| 5% | 0.55 | <.0001* |
| 4% | 0.233 | <.0001* |
| 3% | 0.147 | <.0001* |
| 2% | 0.077 | 0.0003* |
| 1% | −0.01 | 0.1100 |
| 0% | −0.1 | 1.0000 |

Positive values show pairs of means that are significantly different.

TABLE 6

| Study 1 LSD (Least Significant Difference) Threshold Matrix Replicate 2 | | |
|---|---|---|
| Level | Abs(Dif)-LSD | p-Value |
| 20% | 3.807 | <.0001* |
| 10% | 1.274 | <.0001* |
| 8% | 0.92 | <.0001* |
| 5% | 0.674 | <.0001* |
| 6% | 0.617 | <.0001* |
| 4% | 0.394 | <.0001* |
| 2% | 0.174 | <.0001* |
| 3% | 0.144 | <.0001* |
| 1% | −0.05 | 0.5959 |
| 0% | −0.11 | 1.0000 |

Positive values show pairs of means that are significantly different.

TABLE 7

| Study 1 LSD (Least Significant Difference) Threshold Matrix Replicate 3 | | |
|---|---|---|
| Level | Abs(Dif)-LSD | p-Value |
| 20% | 4.284 | <.0001* |
| 10% | 1.37 | <.0001* |
| 8% | 1.2 | <.0001* |
| 3% | 0.124 | 0.0001* |
| 2% | 0.034 | 0.0088* |
| 1% | −0.09 | 0.9997 |
| 0% | −0.11 | 1.0000 |

Positive values show pairs of means that are significantly different.

Bulls A and B Summary: Across all three replicates, using the methodology described above, contamination above 1% was able to be detected.

A second validation study was performed using the same methodology except with Bull C and Bull D.

Figure 12:
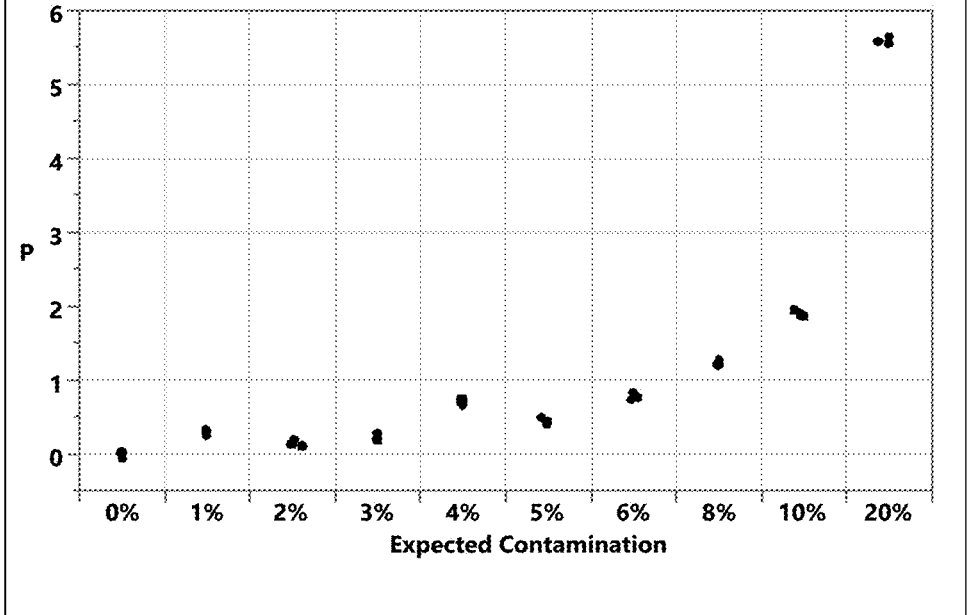
FIG. 12 shows a plot of P values at various levels of contamination for a first replicate using sperm from Bull C and Bull D.
Figure 13:
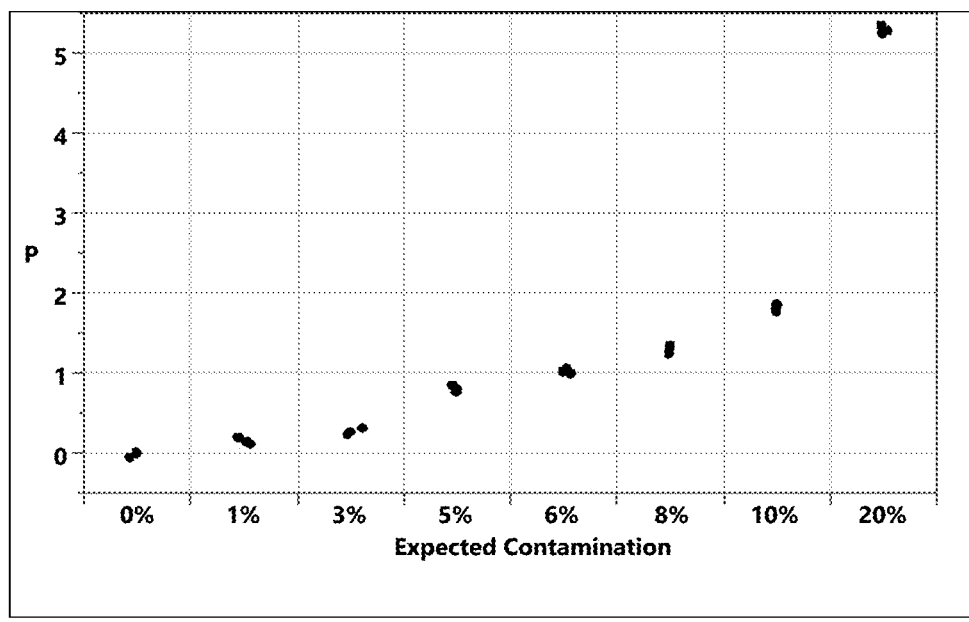
FIG. 13 shows a plot of P values at various levels of contamination for a second replicate using sperm from Bull C and Bull D.
Figure 14:
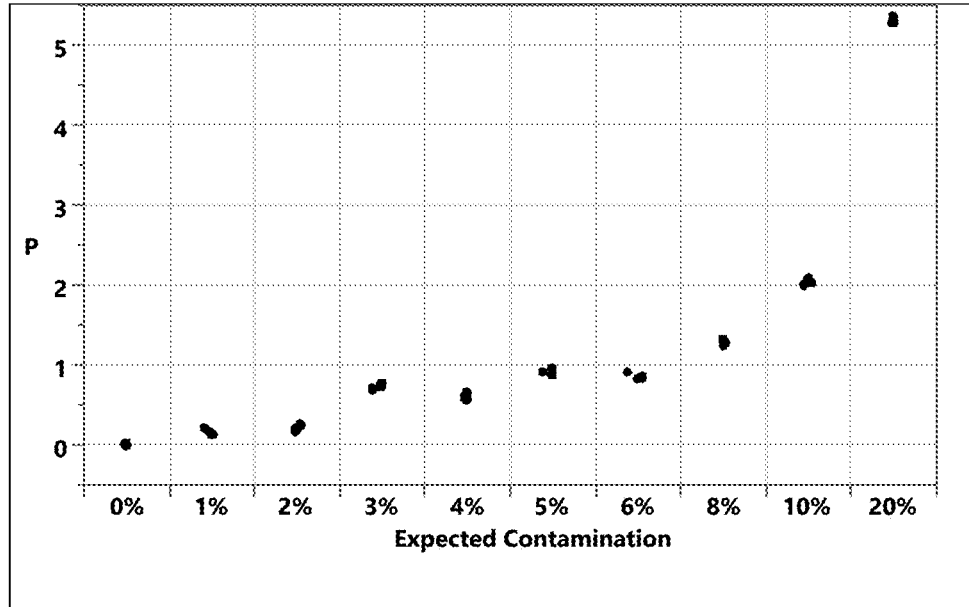
FIG. 14 shows a plot of P values at various levels of contamination for a third replicate using sperm from Bull C and Bull D.

FIGS. 12, 13 and 14 show the scatter plots of P by expected contamination level and replicate for this second study. FIG. 12 shows replicate 1, FIG. 13 shows replicate 2 and FIG. 14 shows replicate 3.

Tables 8, 9 and 10 below show the result of means comparisons for replicates 1, 2 and 3, respectively, in which calculated P values were compared with a control using Dunnett's Method, in which the Control Group=0% contamination.

TABLE 8

| Study 2 LSD (Least Significant Difference) Threshold Matrix Replicate 1 | | |
|---|---|---|
| Level | Abs(Dif)-LSD | p-Value |
| 20% | 5.493 | <.0001* |
| 10% | 1.796 | <.0001* |

TABLE 8-continued

| Study 2 LSD (Least Significant Difference) Threshold Matrix Replicate 1 | | |
|---|---|---|
| Level | Abs(Dif)-LSD | p-Value |
| 8% | 1.129 | <.0001* |
| 6% | 0.673 | <.0001* |
| 4% | 0.603 | <.0001* |
| 5% | 0.343 | <.0001* |
| 1% | 0.183 | <.0001* |
| 3% | 0.123 | <.0001* |
| 2% | 0.043 | 0.0054* |
| 0% | −0.13 | 1.0000 |

Positive values show pairs of means that are significantly different.

TABLE 9

| Study 2 LSD (Least Significant Difference) Threshold Matrix Replicate 2 | | |
|---|---|---|
| Level | Abs(Dif)-LSD | p-Value |
| 20% | 5.211 | <.0001* |
| 10% | 1.728 | <.0001* |
| 8% | 1.214 | <.0001* |
| 6% | 0.944 | <.0001* |
| 5% | 0.718 | <.0001* |
| 3% | 0.188 | <.0001* |
| 1% | 0.068 | 0.0015* |
| 0% | −0.12 | 1.0000 |

Positive values show pairs of means that are significantly different.

TABLE 10

| Study 2 LSD (Least Significant Difference) Threshold Matrix Replicate 3 | | |
|---|---|---|
| Level | Abs(Dif)-LSD | p-Value |
| 20% | 5.203 | <.0001* |
| 10% | 1.923 | <.0001* |
| 8% | 1.166 | <.0001* |
| 5% | 0.803 | <.0001* |
| 6% | 0.75 | <.0001* |
| 3% | 0.62 | <.0001* |
| 4% | 0.493 | <.0001* |
| 2% | 0.09 | 0.0002* |
| 1% | 0.053 | 0.0021* |
| 0% | −0.11 | 1.0000 |

Positive values show pairs of means that are significantly different.

Bulls C and D Summary: Across all three replicates, using the methodology described above, contamination above 1% was able to be detected.

We claim:

1. A method of screening a biological sample for contamination comprising:

sequencing a first biological sample at a first depth to generate a first nucleotide sequence;

determining map coordinates for one or more high confidence homozygous loci (HCHL) in the first nucleotide sequence;

sequencing a second biological sample at a second depth to generate a second nucleotide sequence, wherein the second depth is lower than the first depth;

identifying a nucleotide in the second nucleotide sequence at the determined map coordinates; and comparing a nucleotide in the one or more HCHL in the first nucleotide sequence with the identified nucleotide in the second nucleotide sequence.

2. The method of claim 1, further comprising the step of detecting a mismatch between the nucleotide in the one or more HCHL in the first nucleotide sequence and the identified nucleotide in the second nucleotide sequence.

3. The method of claim 2, further comprising the step of discarding the second biological sample based on the mismatch.

4. The method of claim 1, further comprising the steps of detecting a match between the nucleotide in the one or more HCHL in the first nucleotide sequence and the identified nucleotide in the second nucleotide sequence; and further processing the second biological sample based on the match.

5. The method of claim 4, wherein the second biological sample comprises a sperm cell sample and wherein the step of further processing the second biological sample comprises sex-sorting the second biological sample, ablating sperm cells bearing an undesired sex chromosome in the second biological sample or cryopreserving sperm cells in the second biological sample.

6. The method of claim 1, wherein the first biological sample comprises a pure biological sample.

7. The method of claim 6, wherein the second biological sample comprises a test biological sample.

8. A method of screening a biological sample for contamination comprising:

sequencing a first biological sample at a first depth to generate a first nucleotide sequence;

determining map coordinates for one or more high confidence homozygous loci (HCHL) in the first nucleotide sequence;

sequencing a second biological sample at a second depth to generate a second nucleotide sequence, wherein the second depth is lower than the first depth;

sequencing at least one replicate of the first biological sample at the second depth to generate a third nucleotide sequence;

identifying a nucleotide in the second nucleotide sequence at the determined map coordinates and a nucleotide in the third nucleotide sequence at the determined map coordinates; and comparing a nucleotide in the one or more HCHL in the first nucleotide sequence with i) the identified nucleotide in the second nucleotide sequence and ii) the identified nucleotide in the third nucleotide sequence.

9. The method of claim 8, wherein the step of identifying a nucleotide in the second nucleotide sequence at the determined map coordinates and a nucleotide in the third nucleotide sequence at the determined map coordinates comprises generating read data from the second nucleotide sequence and read data from the third nucleotide sequence; and mapping the read data from the second nucleotide sequence and the read data from the third nucleotide sequence.

10. The method of claim 8, further comprising the step of detecting a mismatch between the nucleotide in the one or more HCHL in the first nucleotide sequence and i) the identified nucleotide in the second nucleotide sequence or ii) the identified nucleotide in the third nucleotide sequence.

11. The method of claim 10, further comprising the step of discarding the second biological sample based on the mismatch.

12. The method of claim 8, further comprising the steps of detecting a match between the nucleotide in the one or more HCHL in the first nucleotide sequence and i) the identified nucleotide in the second nucleotide sequence or ii) the identified nucleotide in the third nucleotide sequence; and further processing the second biological sample based on the match.

13. The method of claim 12, wherein the second biological sample comprises a sperm cell sample and wherein the step of further processing the second biological sample comprises sex-sorting the second biological sample, ablating sperm cells bearing an undesired sex chromosome in the second biological sample or cryopreserving sperm cells in the second biological sample.

14. The method of claim 8, wherein the first biological sample comprises a pure biological sample.

15. The method of claim 14, wherein the second biological sample comprises a test biological sample.

16. The method of claim 8, wherein the at least one replicate comprises a biological replicate.

17. The method of claim 16, wherein the biological replicate comprises a portion of a pure biological sample.

18. A method of screening a biological sample for contamination comprising:

determining or imputing a first nucleotide sequence for a first biological sample and a second nucleotide sequence for a second biological sample, the first biological sample and the second biological sample being from the same individual of a species;

identifying matched and mismatched high confidence homozygous loci (HCHL) between the first nucleotide sequence and the second nucleotide sequence;

determining a matched HCHL count and a mismatched HCHL count from the identified matched and mismatched HCHL, wherein a sum of the matched HCHL count and the mismatched HCHL count constitutes a total HCHL count;

calculating a ratio of the matched HCHL count to the total HCHL count or a ratio of the mismatched HCHL count to the total HCHL count.

* * * * *